United States Patent
Nishikawa et al.

(10) Patent No.: US 8,900,812 B2
(45) Date of Patent: *Dec. 2, 2014

(54) METHOD FOR IDENTIFYING POLYMORPHISM OF NUCLEIC ACID MOLECULES

(71) Applicant: Olympus Corporation, Tokyo (JP)

(72) Inventors: Kazutaka Nishikawa, Tokyo (JP); Hidetaka Nakata, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/946,059

(22) Filed: Jul. 19, 2013

(65) Prior Publication Data

US 2014/0004519 A1   Jan. 2, 2014

Related U.S. Application Data

(63) Continuation of application No. PCT/JP2012/051625, filed on Jan. 26, 2012.

(30) Foreign Application Priority Data

Jan. 26, 2011   (JP) .............................. 2011-014064

(51) Int. Cl.
*C12Q 1/68* (2006.01)
*G01N 21/64* (2006.01)

(52) U.S. Cl.
CPC .......... *C12Q 1/6818* (2013.01); *G01N 21/6452* (2013.01); *G01N 21/6428* (2013.01); *C12Q 1/6827* (2013.01)
USPC ...................................................... 435/6.11

(58) Field of Classification Search
CPC ............... C12Q 1/6827; C12Q 1/6886; G01N 21/6428; G01N 21/6452
See application file for complete search history.

(56) References Cited

U.S. PATENT DOCUMENTS

| | | | |
|---|---|---|---|
| 4,251,733 A | 2/1981 | Hirleman, Jr. | |
| 5,866,336 A | 2/1999 | Nazarenko et al. | |
| 6,280,960 B1 | 8/2001 | Carr | |
| 6,376,843 B1 | 4/2002 | Palo | |
| 6,388,746 B1 | 5/2002 | Eriksson et al. | |
| 6,388,788 B1 | 5/2002 | Harris et al. | |
| 6,400,487 B1 | 6/2002 | Harris et al. | |
| 6,403,338 B1 | 6/2002 | Knapp et al. | |
| 6,710,871 B1 | 3/2004 | Goix | |
| 6,856,391 B2 | 2/2005 | Garab et al. | |
| 6,927,401 B1 | 8/2005 | Palo | |
| 7,015,018 B1 | 3/2006 | Lee et al. | |
| 8,284,484 B2 | 10/2012 | Hoult et al. | |
| 2001/0035954 A1 | 11/2001 | Rahn et al. | |
| 2002/0008211 A1 | 1/2002 | Kask | |
| 2002/0036775 A1 | 3/2002 | Wolleschensky et al. | |
| 2003/0008296 A1 | 1/2003 | Hori et al. | |
| 2003/0036855 A1 | 2/2003 | Harris et al. | |
| 2003/0218746 A1 | 11/2003 | Sampas | |
| 2004/0022684 A1 | 2/2004 | Heinze et al. | |
| 2004/0051051 A1 | 3/2004 | Kato et al. | |
| 2004/0150880 A1 | 8/2004 | Nakata et al. | |
| 2005/0179892 A1 | 8/2005 | Gerstner et al. | |
| 2005/0260660 A1 | 11/2005 | van Dongen et al. | |
| 2006/0078998 A1 | 4/2006 | Puskas et al. | |
| 2006/0158721 A1 | 7/2006 | Nakata et al. | |
| 2006/0256338 A1 | 11/2006 | Gratton et al. | |
| 2008/0052009 A1 | 2/2008 | Chiu et al. | |
| 2009/0159812 A1 | 6/2009 | Livingston | |
| 2010/0033718 A1 | 2/2010 | Tanaami | |
| 2010/0177190 A1 | 7/2010 | Chiang et al. | |
| 2010/0202043 A1 | 8/2010 | Ujike | |

FOREIGN PATENT DOCUMENTS

| | | |
|---|---|---|
| EP | 1580586 A1 | 9/2005 |
| EP | 1 906 172 A1 | 4/2008 |
| JP | 04-337446 A | 11/1992 |
| JP | 2002-507762 A | 3/2002 |
| JP | 2002-543414 A | 12/2002 |
| JP | 2003-506068 A | 2/2003 |
| JP | 2004-506192 A | 2/2004 |
| JP | 2004-187581 A | 7/2004 |
| JP | 2005-098876 A | 4/2005 |

(Continued)

OTHER PUBLICATIONS

Meyer-Almes, F.J, "A new Method for Use in Molecular Diagnostics and High Throughput Pharmaceutical Screening based on Fluorescence Correlation Spectroscopy", Nanoparticle Immunoassays, R. Rigler, edit, Springer, Berlin, 2000, pp. 204-224. Cited in specification.

(Continued)

*Primary Examiner* — James Martinell
(74) *Attorney, Agent, or Firm* — Westerman, Hattori, Daniels & Adrian, LLP

(57) ABSTRACT

The present invention provides a method for identifying polymorphism of nucleic acids in a sample solution in which the concentration or number density of the observed nucleic acids is lower than that of conventional photometric analysis technologies. It includes: preparing a sample solution comprising a first nucleic acid probe, which specifically hybridizes with a single-stranded nucleic acid molecule including a first type of base sequence, and a target nucleic acid molecule; forming a hybrid of the nucleic acid molecules in the sample solution; calculating a number of molecules of the hybrid including the first nucleic acid probe in the sample solution by the scanning molecule counting method; and identifying polymorphism of the target nucleic acid molecule based on the calculating result. The sample solution includes an oligonucleotide having a base sequence complementary to a base sequence different from the first type of base sequence in the polymorphic sequence.

13 Claims, 10 Drawing Sheets

(56) References Cited

FOREIGN PATENT DOCUMENTS

| | | |
|---|---|---|
| JP | 2005-099662 A | 4/2005 |
| JP | 2007-20565 A | 2/2007 |
| JP | 4023523 B2 | 12/2007 |
| JP | 2008-116440 A | 5/2008 |
| JP | 2008-173015 A | 7/2008 |
| JP | 2008-536093 A | 9/2008 |
| JP | 2008-292371 A | 12/2008 |
| JP | 2009-145242 A | 7/2009 |
| JP | 2009-281831 A | 12/2009 |
| JP | 2009-288161 A | 12/2009 |
| JP | 2011-002415 A | 1/2011 |
| WO | 98/16814 A1 | 4/1998 |
| WO | 99/47963 A1 | 9/1999 |
| WO | 00/66985 A1 | 11/2000 |
| WO | 01/73120 A1 | 10/2001 |
| WO | 02/12864 A1 | 2/2002 |
| WO | 2006/084283 A2 | 8/2006 |
| WO | 2007/010803 A1 | 1/2007 |
| WO | 2007/147159 A2 | 12/2007 |
| WO | 2008/007580 A1 | 1/2008 |
| WO | 2008/080417 A1 | 7/2008 |
| WO | 2009/117033 A2 | 9/2009 |
| WO | 2011/108369 A1 | 9/2011 |
| WO | 2011/108370 A1 | 9/2011 |
| WO | 2011/108371 A1 | 9/2011 |
| WO | 2012/014778 A1 | 2/2012 |

OTHER PUBLICATIONS

Katoh, N. et al., "A single molecule analyzer that enable new analysis of DNA and protein interactions", Genetic Medicine, vol. 6, No. 2, 2002, pp. 271-277. Cited in specification.
Tyagi, S. et al., "Molecular Beacons: Probes that Fluoresce upon Hybridiation", Nature Biotrchnology, 1996, vol. 14, pp. 303-308. Cited in specification.
Giesendorf, B. A.J. et al., "Molecular beacons: a New Approach for Semiautomated Mutation Analysis" Clinical Chemistry, 1998, vol. 44, No. 3, pp. 482-486. Cited in Specification.
Howell, W. M. et al., "iFRET: An Improved Fluorescence System for DNA-Melting Analysis", Genome Resaerch, 2002, vol. 12, pp. 1401-1407. Cited in specification.
Takatsu K. et al., "A FRET-based Analysis of SNPs without fluorescent probes", Nucleic Acid resaerch, 2004, vol. 32, No. 19, e156. Cited in specification.
Kinjo M., "Single Molecule Detection by fluorescence Correlation Spectroscopy", Proteins, Nucleic Acids and Enzymes, 1999, vol. 44, No. 9, pp. 1431-1438. Cited in Specification.
International Search report for PCT/JP2012/051416, Mailing Date of Apr. 10, 2012.
International Search reaport for PCT/JP2012/51625, Mailing Date of Mar. 13, 2012.
Park, Mira et al., "Counting the Number of Fluorophores Labeled in Biomolecules by Observing the Fluorescence-Intensity of a Single Molecule" Bulletin of the Chemical Society of Japan, dated Aug. 30, 2005, vol. 78, No. 9, p. 1612-1618.
U.S. Office Action dated Apr. 2, 2013, issued in related U.S. Appl. No. 13/596,280 (13 pages).
Kask, Peet et al., "Two-Dimensional Fluorescence Intensity Distribution Analysis: Theory and Applications", Biophysical Journal, Apr. 2000, vol. 78, p. 1703-1713.
Chinese Office Action dated Aug. 13, 2013, issued in related Chinese application No. 201180011655.3; w/ English Translation (16 pages).
International Search Report dated Mar. 29, 2011, issued in related PCT/JP2011/053483.
International Preliminary Report on Patentability (PCT/IPEA/409) issued in related PCT/JP2011/053483 (2012).
Chinese Office Action dated Aug. 9, 2013, issued in related Chinese application No. 201180011640.7; w/ English Translation (16 pages).
International Search Report dated Mar. 29, 2011, issued in related PCT/JP2011/053482.

International Preliminary Report on Patentability (PCT/IPEA/409) issued in related PCT/JP2011/053482 (Mar. 29, 2011).
Notice of Allowance dated Mar. 27, 2013, issued in related U.S. Appl. No. 13/597,825 (8 pages).
Chinese Office Action dated Feb. 7, 2013, issued in related Chinese application No. 201180011644.5; w/ English Translation (18 pages).
Extended European Search Report dated Mar. 28, 2013, issued in related EP application No. 11750481.1.
International Search Report dated Mar. 29, 2011, issued in related PCT/JP2011/053481.
International Preliminary Report on Patentability (PCT/IPEA/409) issued in related PCT/JP2011/053481 (2011).
Goodwin, Peter et al., "Rapid Sizing of Individual Fluorescently Stained DNA Fragments by Flow Cytometry," Nucleic Acids Research, 1993, vol. 21, No. 4, p. 803-806.
Keller, Richard et al., "Single-Molecule Fluorescence Analysis in Solution," Applied Spectroscopy, 1996, vol. 50, No. 7, p. 12A-32A.
Lee, Yuan-Hsiang et al., "Laser-Induced Fluorescence Detection of a Single Molecule in a Capillary," Analytical Chemistry, dated Dec. 1, 1994, vol. 66, No. 23, p. 4142-4149.
Li, Haitao et al., "Ultrasensitive Coincidence Fluorescence Detection of Single DNA Molecules," Analytical Chemistry, dated Apr. 1, 2003, vol. 75, No. 7, p. 1664-1670.
Nie, Shuming et al., "Probing Individual Molecules with Confocal Fluorescence Microscopy," Science, dated Nov. 11, 1994, vol. 266, p. 1018-1021.
Tahari, Abdel. "Fluorescence Correlation Spectroscopy: Ultrasensitive Detection in Clear and Turbid Media," University of Illinois, 2006, p. 1-88.
Wu, Alan et al., "Development and Preliminary Clinical Validation of a High Sensitivity Assay for Cardiac Troponin Using a Capillary Flow (Single Molecule) Fluorescence Detector," Clinical Chemistry, 2006, vol. 52, No. 11, p. 2157-2159.
Itoh et al., "A New Method for Detection of Influenza Viruses by Single Particle-Recognition Based on the Principle of Fluorescence Correlation Spectroscopy," Chemistry and Biology, 2009, vol. 47, No. 12, p. 823-830 Title only.
Carlsson, K. et al., "Three-dimensional Microscopy Using a Confocal Laser Scanning Microscope", Optics Letters, Optical Society of America, Feb. 1985, vol. 10, No. 2, p. 53-55, XP007922413.
U.S. Office Action dated Oct. 4, 2013, issued in related U.S. Appl. No. 13/596,243 (15 pages).
Japanese Office Action dated Dec. 18, 2012 issued in related JP application No. 2012-503060; w/ English Translation (6 pages).
Sando, Shinsuke et al. "Quencher as Leaving Group: Efficient Detection of DNA-Joining Reactions", Journal of the American Chemical Society, 2002, vol. 124, No. 10, p. 2096-2097.
Kask, Peet et al. "Fluorescence-Intensity Distribution Analysis and its Application in Biomolecular Detection Technology", PNAS, Nov. 23, 1999, vol. 96, No. 24, p. 13756-13761.
International Search Report dated Sep. 20, 2011, issued in related PCT/JP2011/066576.
U.S. Office Action dated Feb. 20, 2014, issued in related U.S. Appl. No. 13/746,968 (11 pages).
U.S. Office Action dated Jun. 12, 2014, issued in related U.S. Appl. No. 13/944,550 (6 pages).
U.S. Office Action dated May 22, 2014, issued in related U.S. Appl. No. 13/746,968 (10 pages).
U.S. Office Action dated Jan. 3, 2013, issued in related U.S. Appl. No. 13/597,825 (5 pages).
Doyon, Jeffrey et al., "Highly Sensitive in Vitro Selections for DNA-Linked Synthetic Small Molecules with Proteins Binding Affinity and Specificity", Journal of the American Chemical Society, 2003, vol. 125, No. 41, p. 12372-12373.
Marme, N. et al., "Identification of Single-Point Mutations in Mycobacterial 16S rRNA Sequences by Confocal Single-Molecule Fluorescence Spectroscopy," Nucleic Acids Research, 2006, vol. 34, No. 13, p. e90-e90.
Bentolila, L. A. et al., "Single-Step Multicolor Fluorescence in Situ Hybridization Using Semiconductor Quantum Dot-DNA Conjugates," Cell Biochemistry and Biophysics, 2006, vol. 45, p. 59-70.

(56) References Cited

OTHER PUBLICATIONS

Kato, N. et al., "A Single Molecule Analyzer that Enables New Analysis of DNA and Protein Interactions," Gene & Medicine, 2002, vol. 6, No. 2 (Concise English Explanation).

Itoh, M et al., "A New Method for Detection of Influenza Viruses by Single Particle-Recognition Based on the Principle of Fluorescence Correlation Spectroscopy," Chemistry and Biology, 2009, vol. 47, No. 12 (Concise English Explanation).

Extended European Search Report dated Aug. 20, 2014, issued in related EP application No. 12739756.0.

FIG. 14
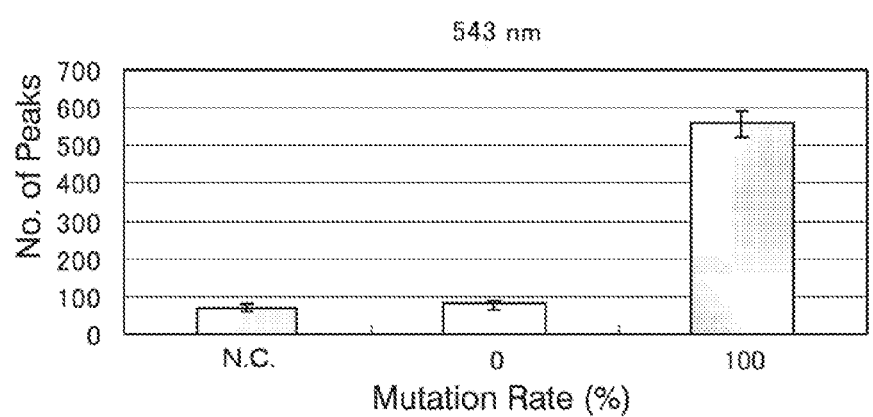
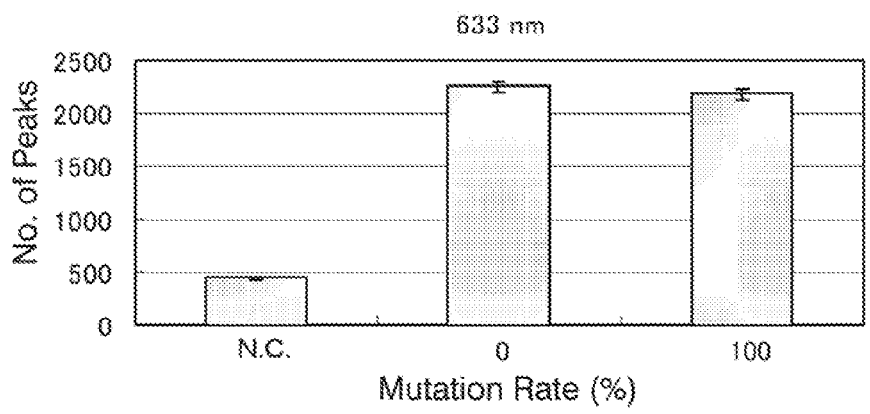

METHOD FOR IDENTIFYING POLYMORPHISM OF NUCLEIC ACID MOLECULES

The present application is a U.S. Continuation-in-part application based on the PCT International Patent Application, PCT/JP2012/051625, filed on Jan. 26, 2012, the contents of which are incorporated herein by reference.

TECHNICAL FIELD

The present invention relates to a method for identifying nucleic acids having similar base sequences in the manner of genetic polymorphisms such as somatic mutations or single nucleotide polymorphisms using optics capable of detecting light from a microregion in a solution such as the optics of a confocal microscope or multiphoton microscope.

The present application claims priority on the basis of Japanese Patent Application No. 2011-014064 filed in Japan on Jan. 26, 2011, the contents of which are incorporated herein by reference.

BACKGROUND ART

Numerous methods have been reported for detecting nucleic acids having a specific base sequence that consist of investigating the base sequence of a nucleic acid using artificially synthesized short-stranded oligonucleotides such as probes or primers. In particular, various techniques using fluorescent light have been developed based on its superior detection sensitivity in genetic analyses such as analyses of somatic mutations and single nucleotide polymorphisms.

One example of a method for identifying nucleic acids using an FRET probe is a so-called molecular beacon method that uses a single-stranded nucleic acid having mutually complementary base sequences on the 5'-terminal side and 3'-terminal side and in which both ends are labeled with a fluorescent substance and a quenching substance, respectively (molecular beacon probe) (see, for example, Tyagi, et al., Nature Biotechnology, 1996, Vol. 14, pp. 303-308). Although a quenched state results due to conjugation of both ends resulting in the formation of an intramolecular loop in the case only the molecular beacon is present; as a result of hybridizing with a target nucleic acid, the intramolecular loop is unlocked resulting in the emission of fluorescent light. Genetic polymorphisms can be identified by using a molecular beacon that specifically hybridizes with a specific genotype among genetic polymorphisms (see, for example, Giesendorf, et al., Clinical Chemistry, 1998, Vol. 44, No. 3, pp. 482-486).

In addition, there are also methods that detect nucleic acids using a FRET probe obtained from a fluorescent intercalator and fluorescent probe (see, for example, Howell, et al., Genome Research, 2002, Vol. 12, pp. 1401-1407). In these methods, a probe labeled with a fluorescent substance hybridizes with another single-stranded nucleic acid, and a fluorescent intercalator is inserted between the base pairs of the double-stranded nucleic acid formed. By using FRET that occurs between the fluorescent intercalator and the fluorescent substance used to label the fluorescent probe, a distinction can be made between the fluorescent probe when present alone and the fluorescent probe that forms a double-stranded nucleic acid. By using this principle, genetic polymorphisms can be identified by labeling a probe that specifically hybridizes with a specific genotype among genetic polymorphisms and a probe that specifically hybridizes with another genotype with respectively different fluorescent substances, and then detecting FRET occurring between each of the fluorescent substances and a fluorescent intercalator (see, for example, Takatsu, et al., Nucleic Acid Research, 2004, Vol. 32, No. 19, e156).

On the other hand, due to the advancement of photometric technology in recent years, it has become possible to detect and measure faint light at the level of a single photon or single fluorescent molecule using confocal microscope optics and ultra-high sensitivity photodetection technologies capable of photon counting (detection of individual photons). Various devices or methods have been proposed for detecting molecular interaction, or bonding and dissociation reactions of biomolecules using these technologies for measuring faint light. For example, in the case of fluorescent correlation spectroscopy (FCS: see, for example, Japanese Unexamined Patent Application, First Publication No. 2005-098876, Japanese Unexamined Patent Application, First Publication No. 2008-292371, Kaneshiro, M., Proteins, Nucleic Acids and Enzymes, 1999, Vol. 44, No. 9, pp. 1431-1438, Mayer-Alms, Fluorescence Correlation Spectroscopy, R. Rigler, ed., Springer, Berlin, 2000, pp. 204-224, and Katoh, N. et al., Genetic Medicine, 2002, Vol. 6, No. 2, pp. 271-277), laser confocal microscope optics and photon counting technology are used to measure fluorescence intensity from fluorescent molecules or fluorescence-labeled molecules (fluorescence-labeled molecules or the like) that enter and leave a microregion in a sample solution (focal region where laser light from a microscope is concentrated, also referred to as confocal volume). Information such as the speed of movement, size or concentration of fluorescent molecules and the like can be acquired, or various phenomena can be detected, including changes in molecular structure or size, molecular bonding and dissociation reactions, dispersion and aggregation, based on the average retention time (translational diffusion time) of fluorescent molecules and the average value of the number of molecules remaining in the microregion determined from the value of the autocorrelation function of the measured fluorescence intensity. In addition, in the case of fluorescence intensity distribution analyses (FIDA: see, for example, Japanese Patent No. 4023523) and photon counting histograms (PCH: see, for example, International Publication No. WO 2008/080417), a histogram is generated of the fluorescence intensity of fluorescent molecules and the like that enter and leave a confocal volume measured in the same manner as FCS, and the average value of brightness characteristic to those fluorescent molecules and the average value of the number of molecules remaining in the confocal volume are calculated by fitting a statistical model to the distribution of that histogram. Changes in molecular structure or size, bonding and dissociated states, dispersion, aggregation and the like are then estimated based on this information. Moreover, Japanese Unexamined Patent Application, First Publication No. 2007-20565 and Japanese Unexamined Patent Application, First Publication No. 2008-116440 propose a method for detecting a fluorescent substance based on the elapsed time of a fluorescent signal of a sample solution measured using confocal microscope optics. Japanese Unexamined Patent Application, First Publication No. H4-337446 proposes a signal arithmetic processing technology for detecting the presence of fluorescent microparticles in a flow or on a substrate by using photon counting technology to measure faint light from fluorescent microparticles that have passed by a flow cytometer or from fluorescent microparticles immobilized on the substrate.

In particular, according to methods employing technologies for measuring fluorescence in a microregion using confocal microscope optics and photon counting technology in the manner of FCS or FIDA and the like, the sample required for measurement is of a much lower concentration and extremely small amount in comparison with in the past (the amount used for a single measurement is at most about several tens of microliters), and measurement time is shortened considerably (measurements taking only several seconds per measurement can be repeated several times). Thus, these technologies are expected to be powerful tools for enabling experimentation or testing to be carried out inexpensively or rapidly in comparison with conventional biochemical methods particularly in the case of carrying out analyses on scarce or expensive samples frequently used in medical, biological and other research and development fields, or in the case of large numbers of specimens as in the clinical diagnosis of diseases or screening for physiologically active substances.

SUMMARY OF THE INVENTION

The present invention is related to a method for identifying polymorphism of nucleic acid molecules in a sample by detecting a hybrid with the nucleic acid probe using a scanning molecule counting method. In the method for identifying polymorphism of nucleic acid molecules, polymorphism of nucleic acid molecules is identified based on the presence or absence of the formation of a hybrid with a nucleic acid probe by using a nucleic acid probe that specifically hybridizes with one type of nucleic acid molecule in a polymorphic sequence. In this method, the hybrid forming reaction between the nucleic acid probe and the nucleic acid molecules in the sample is performed, and the hybrid is detected by the scanning molecule counting method in the presence of the oligonucleotide (decoy nucleic acid) including a base sequence complementary to a base sequence different from the first type of base sequence in the polymorphic sequence.

Here, the scanning molecule counting method refers to a novel photometric analysis technology proposed by the present applicant in Japanese Patent Application No. 2010-044714.

The present invention has aspects indicated below.

(1) A method for identifying polymorphism of nucleic acid molecules including:

(a) a step of preparing a sample solution comprising a first nucleic acid probe, which specifically hybridizes with a single-stranded nucleic acid molecule including a first type of base sequence in a polymorphic sequence, and a target nucleic acid molecule;

(b) a step of forming a hybrid of the nucleic acid molecules in the sample solution prepared in (a);

(c) a step of calculating a number of molecules of the hybrid including the first nucleic acid probe in the sample solution prepared in (a) after carrying out (b);

(d) a step of identifying polymorphism of the target nucleic acid molecule based on a result of (c);

(e) a step of moving a location of a photodetection region of an optics system in the sample solution in (c) using an optics system of a confocal microscope or a multiphoton microscope;

(f) a step of detecting fluorescence emitted from the hybrid in the photodetection region while moving the location of the photodetection region of the optics system in the sample solution in (c);

(g) a step of individually detecting the hybrid in (c) by individually detecting an optical signal from each hybrid among the detected fluorescent light; and (h) a step of counting a number of particles detected during movement of the location of the photodetection region in (c) by counting the number of individually detected hybrid, wherein the sample solution in (a) or the sample solution after (b) and before (c) includes an oligonucleotide having a base sequence complementary to a base sequence different from the first type of base sequence in the polymorphic sequence.

(2) The method for identifying polymorphism of nucleic acid molecules according to (1) shown above, wherein the first nucleic acid probe is labeled by a fluorescent substance.

(3) The method for identifying polymorphism of nucleic acid molecules according to (1) or (2) shown above, wherein the sample solution in (a) further includes a fluorescent double-stranded nucleic acid-binding substance that binds specifically to double-stranded nucleic acids.

(4) The method for identifying polymorphism of nucleic acid molecules according to (2) shown above, wherein the sample solution in (a) further includes a fluorescent double-stranded nucleic acid-binding substance, at least one of the fluorescent substance used to label the first nucleic acid probe and the fluorescent double-stranded nucleic acid-binding substance is a fluorescent substance serving as an energy donor in a fluorescent energy transfer phenomenon, while the other is a substance serving as an energy acceptor in a fluorescent energy transfer phenomenon, and the fluorescence emitted from the hybrid including the first nucleic acid probe in (c) is fluorescence emitted by a fluorescent energy transfer phenomenon occurring between the fluorescent substance used to label the first nucleic acid probe and the fluorescent double-stranded nucleic acid-binding substance.

(5) The method for identifying polymorphism of nucleic acid molecules according to (2) shown above, wherein the first nucleic acid probe is bound to a fluorescent substance serving as an energy donor and a substance serving as an energy acceptor so that fluorescent energy transfer occurs when the probe is present alone, and fluorescent energy transfer does not occur when the probe hybridizes with another single-stranded nucleic acid molecule, and the fluorescence emitted from the hybrid including the nucleic acid probe is fluorescence that is emitted from the fluorescent substance serving as an energy donor.

(6) The method for identifying polymorphism of nucleic acid molecules according to any one of (1) to (5) shown above, wherein the location of the photodetection region is moved at a predetermined speed in moving the location of a photodetection region.

(7) The method for identifying polymorphism of nucleic acid molecules according to any one (1) to (6) shown above, wherein the location of the photodetection region is moved at a speed faster than a speed of spreading diffusion of the hybrid in moving a location of a photodetection region.

(8) The method for identifying polymorphism of nucleic acid molecules according to any of (1) to (7) shown above, wherein entry of the hybrid into the photodetection region is detected based on a waveform of the optical signal detected chronologically in individually detecting a hybrid by individually detecting an optical signal from each hybrid among the detected fluorescent light.

(9) The method for identifying polymorphism of nucleic acid molecules according to any of (1) to (8) shown above, wherein the sample solution contains one or more of compounds selected from the group consisting of surfactant, formamide, dimethylsulfoxide and urea.

(10) The method for identifying polymorphism of nucleic acid molecules according to any of (1) to (9) shown above, wherein (b) is carried out by hybridizing the nucleic acid molecules in the sample solution by lowering a liquid temperature of the sample solution at a lowering rate of 0.05° C./second or faster after denaturing nucleic acid molecules in the sample solution prepared in step (a) by heating the sample solution to 70° C. or higher.

(11) The method for identifying polymorphism of nucleic acid molecules according to any of (1) to (10) shown above, wherein the first nucleic acid probe is composed by binding two or more molecules selected from the group consisting of DNA, RNA and nucleic acid analogues.

(12) The method for identifying polymorphism of nucleic acid molecules according to any of (1) to (11) shown above, wherein the polymorphic sequence is a base sequence comprising a polymorphic site of a genetic polymorphism or a base sequence comprising a mutation site of a somatic mutation.

(13) The method for identifying polymorphism of nucleic acid molecules according to (12) shown above, wherein the somatic mutation is a mutation of the K-ras gene.

In the scanning molecule counting method used in the method for identifying polymorphism of nucleic acid molecules of an aspect of the present invention (hereinafter referred as "the method for identifying polymorphism of nucleic acid molecules of the present invention"), there is no need to employ statistical processing in the manner of determining fluctuations in fluorescence intensity. Consequently, it is possible to identify polymorphism even in the case where a nucleic acid molecule having a target polymorphic sequence is only present in a trace amount in a sample by using the method for identifying polymorphism of nucleic acid molecules of the present invention.

Furthermore, the detecting of the hybrid of the nucleic acid probe and the nucleic acid molecules in the sample by the scanning molecule counting method is performed in the presence of the oligonucleotide including a base sequence complementary to a base sequence different from the first type of base sequence in the polymorphic sequence. Therefore, non-specific hybridization of the nucleic acid probe to the other type of nucleic acid molecules from the hybridization reaction to the detection can be effectively suppressed. Consequently, polymorphism can be identified very accurately, having the non-specific hybrid formation by the nucleic acid probe being suppressed effectively.

BRIEF DESCRIPTION OF THE DRAWINGS

FIG. 14 is a drawing indicating the values of the number of peaks counted for each GTT mutation rate in target nucleic acid molecules added to sample solutions in Example 6.

DETAILED DESCRIPTION OF THE PREFERRED EMBODIMENTS

Figure 1:
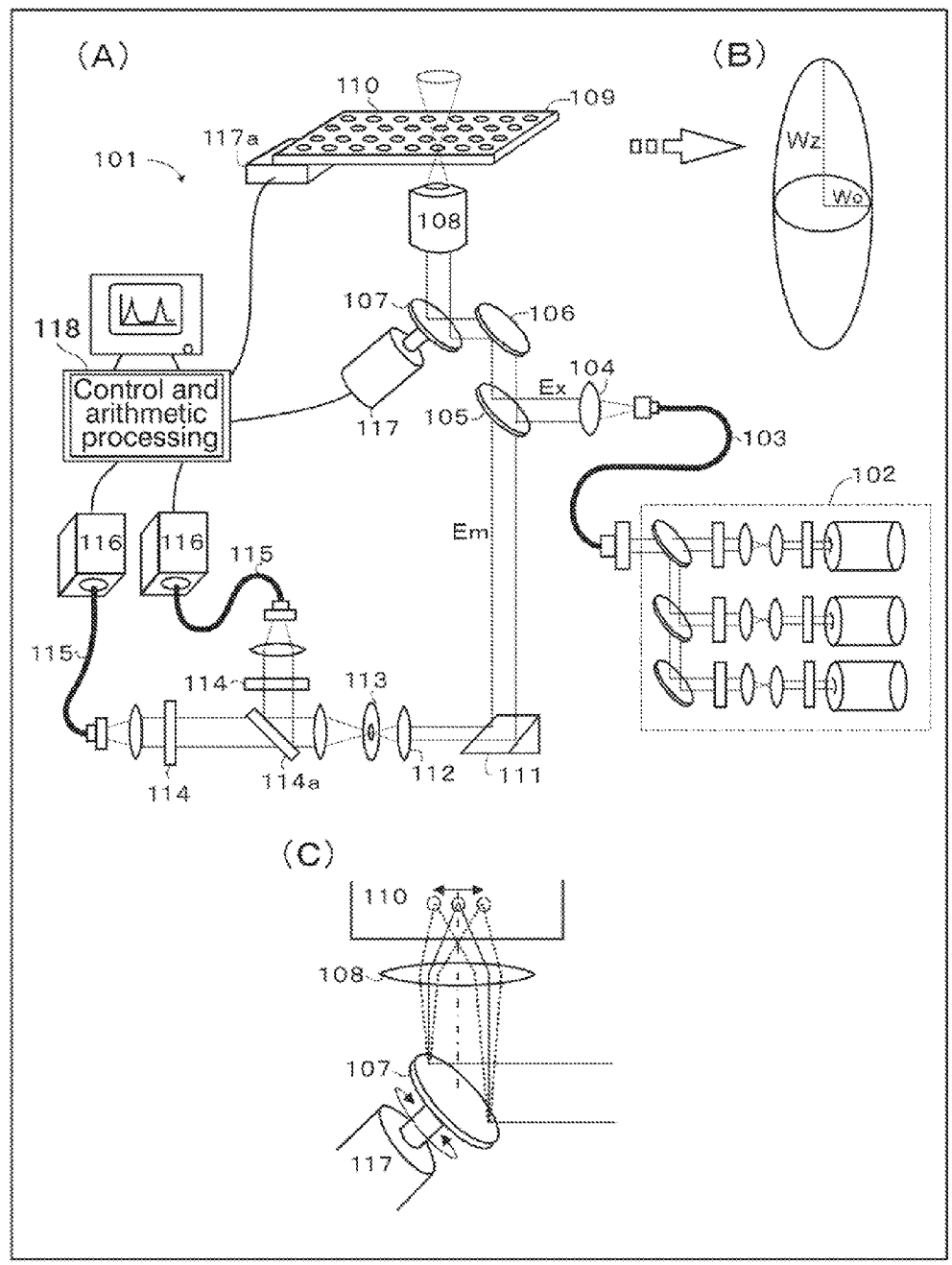
FIG. 1(A) is a schematic diagram of the internal structure of a photometric analysis device for a scanning molecule counting method.
FIG. 1(B) is a schematic diagram of the confocal volume (observed region of a confocal microscope).
FIG. 1(C) is a schematic diagram of a mechanism for moving the location of a photodetection region in a sample solution by changing the orientation of a mirror 107.

An explanation is first provided of a scanning molecule counting method. The scanning molecule counting method is a technology that makes it possible to count luminescent particles or acquire information relating to the concentration or number density of luminescent particles by detecting light emitted from luminescent particles in a microregion when light-emitting particles (luminescent particles) that move randomly when dispersed in a sample solution traverse the microregion while scanning the sample solution according to the microregion, and individually detecting each luminescent particle in the microregion as a result thereof. Similar to photometric analysis technologies in the manner of FIDA and the like, the amount of sample required for measurement may be a trace amount (on the order of, for example, several tens of microliters) and the measurement time is short. Moreover, in comparison with the case of photometric analysis technologies in the manner of FIDA and the like, properties such as concentration or number density of luminescent particles can be detected quantitatively even if they are present at a lower concentration or lower number density.

Luminescent particles refer to particles in which target particles and a luminescent probe are bound or hybridized. A "luminescent probe" refers to a substance that emits light and has the property of binding or conjugating to target particles (normally referred to as molecules or molecular aggregates), and although it is typically a fluorescent particle, it may also be a particle that emits light by phosphorescence, chemiluminescence, bioluminescence or light scattering and the like. The first nucleic acid probe and second nucleic acid probe used in the method for identifying polymorphism of nucleic acid molecules of the present invention are equivalent to luminescent probes.

In the present invention and description of the present application, a "photodetection region" of the optics of a confocal microscope or multiphoton microscope refers to the microregion where light is detected in these microscopes, and in the case illumination light is imparted from an object lens, is equivalent to the region where that illumination light is concentrated. Furthermore, this region is defined according to the positional relationship between the object lens and a pinhole in a confocal microscope in particular.

Light is successively detected while moving the location of the photodetection region in a sample solution, or in other words, while scanning with the photodetection region. When the photodetection region that is moved contains a luminescent probe bound or hybridized to a randomly moving particle, light from the luminescent probe is detected, and as a result thereof, the presence of a single particle is detected (depending on the actual mode of detection, it is also possible that the luminescent probe is initially bound to a particle desired to be detected and then dissociates from the particle when light is detected). Optical signals from the luminescent probe are individually detected in the successively detected light, and as a result thereof, the presence of particles (bound to the luminescent probe) are individually and successively detected one at a time, and various information relating to the state of the particles in the solution is acquired. More specifically, in the aforementioned configuration, for example, the number of particles detected during movement at the location of a photodetection region may be counted by counting the number of individually detected particles (particle counting). According to this configuration, information relating to the number density or concentration of particles in a sample solution is obtained by combining the number of particles and the amount of movement of the location of the photodetection region. In particular, the number density or concentration of particles can be specifically calculated by an arbitrary method, such as by moving the location of the photodetection region at a predetermined speed, if the total volume of the movement locus of the location of the photodetection region is specified. Naturally, instead of determining an absolute number density value or calculation value directly, the ratio of number density or concentration relative to a plurality of sample solutions or a standard sample solution serving as a standard for concentration or number density may also be calculated. In addition, by configuring the scanning molecular counting method so as to move the location of the photodetection region by changing the light path of the optics, movement of the photodetection region is rapid and mechanical vibrations or fluid dynamic action do not substantially occur in the sample solution. Consequently, light can be measured with the target particles in a stable state that is not subjected to the effects of dynamic action (if vibrations or flow act in the sample solution, there is a possibility of a change in the physical properties of the particles). Since a configuration is not required for allowing a sample solution to flow through, sample solutions present in trace amounts (about one to several tens of microliters) can be measured and analyzed in the same manner as the case of FCS or FIDA and the like.

In the aforementioned step for individually detecting particles, a judgment as to whether or not a luminescent probe bound to a single particle (including the case of a single luminescent probe being bound to a single particle, the case of a plurality of luminescent probes being bound to a single particle, and the case of a luminescent probe that has dissociated from a particle after having bound to that single particle according to an experimental mode, and to apply similarly hereinafter) has entered the photodetection region based on successively detected optical signals may be made based on the shape of detected chronological optical signals. In an embodiment, a luminescent probe bound to a single particle may typically be detected as having entered a photodetection region when an optical signal is detected that has intensity greater than that of a threshold value.

In addition, in the aforementioned step for moving the location of the photodetection region, the speed at which the location of the photodetection region is moved in the sample solution is suitably changed based on the properties of the luminescent probe bound to the particles or the number density or concentration in the sample solution. As would be understood by a person with ordinary skill in the art, the mode of light detected from the luminescent probe bound to particles can be changed according to the properties thereof of the number density or concentration in the sample solution. In particular, since the amount of light detected from the luminescent probe bound to the particles decreases if the movement speed of the photodetection region increases, the movement speed of the photodetection region may be suitably changed so that light from a luminescent probe bound to a single particle can be measured accurately or with good sensitivity.

Moreover, in the aforementioned step for moving the location of the photodetection region, the movement speed of the location of the photodetection region in the sample solution may be set to be higher than the spreading diffusion speed (average movement speed of particles due to Brownian motion) of the luminescent probe bound to a detected particle (namely, a hybrid containing the first nucleic acid probe or a hybrid containing the second nucleic acid probe in the method for detecting polymorphism of nucleic acid molecules of the present invention). As was previously explained for the scanning molecule counting method, luminescent probes are individually detected by detecting light emitted from a luminescent probe when a photodetection region has passed a location where that luminescent probe bound to a single particle is present. However, in the case the luminescent probe bound to a particle is moving randomly in the solution due to Brownian movement and enters and leaves the photodetection region multiple times, an optical signal (representing the presence of a particle desired to be detected) originated from a single luminescent probe ends up being detected multiple times, thereby making it difficult to correlate the detected optical signal with the presence of a single particle desired to be detected. Therefore, as was previously described, the movement speed of the photodetection region is set to be higher than the spreading diffusion speed of the luminescent probe bound to a particle (and more specifically, set so as to move at a speed faster than the spreading diffusion speed of a hybrid containing the first nucleic acid probe or a hybrid containing the second nucleic acid probe), and as a result thereof, a luminescent probe bound to a single particle can be correlated with a single optical signal (represent the existence of a particle). Furthermore, since the spreading diffusion speed changes according to the luminescent probe bound to a particle, the movement speed of the photodetection region may be suitably changed corresponding to the properties (and particularly the diffusion constant) of the luminescent probe bound to the particle as was previously described.

The light path of the optics for moving the location of the photodetection region may be changed by an arbitrary method. For example, the location of the photodetection region may be changed by changing the light path using a galvanometer mirror employed in a laser scanning light microscope. The movement locus of the location of the photodetection region may be set arbitrarily, and for example, can be selected from among a circular shape, elliptical shape, rectangular shape, straight line and curve.

Since the photodetection mechanism per se of the scanning molecule counting method is configured so as to detect light from a photodetection region of a confocal microscope or multiphoton microscope in the same manner as in the case of photometric analysis technologies such as FIDA, the amount of sample solution may also similarly be a trace amount. Moreover, since statistical processing involving determination of fluctuations in fluorescence intensity is not carried out in the scanning molecule counting method, the photometric analysis technology of the scanning molecule counting method can be applied sample solutions in which the number density or concentration of particles is at a much lower level than that required by photometric analysis technologies such as FIDA.

In addition, in the scanning molecule counting method, since each particle that has dispersed or dissolved in a solution is detected individually, the particles can be counted quantitatively, the concentration or number density of the particles in a sample solution can be calculated, or information relating to concentration of number density can be acquired by using that information. Namely, according to the scanning molecule counting method, since particles for which particles that pass through a photodetection region and detected optical signals are detected one at a time by correlating on a 1:1 basis, particles randomly moving by dispersing in a solution can be counted, thereby making it possible to determine the concentration or number density of particles in a sample solution more accurately than in the past. In actuality, according to the method for identifying polymorphism of nucleic acid molecules of the present invention in which particle concentration is determined by individually detecting hybrids containing a first nucleic acid probe and the like by counting the number thereof, polymorphic nucleic acids can be identified even if the concentration of these hybrids in a sample solution is lower than the concentration that can be determined based on fluorescence intensity measured with a fluorescence spectrophotometer or plate reader.

Furthermore, according to the aspects of the present invention, in which the scanning is performed in the photodetection region in the sample solution varying the light paths of the optic system, observation is done evenly in the sample solution and in a mechanically stable condition without placing mechanical or hydrodynamic action. Thus, quantitative reliability of the detected results improves relative to the case where physical flow is generated in the sample, for example. When physical flow is generated in the sample, it is difficult to control the flow rate to be consistent. Also, the device configuration becomes complicated. Also, the amount of the sample needed for the analysis increases significantly. Also, it is possible the particles, the luminescent probe or the associated body, or other substances in the solution can be altered or denatured by the hydrodynamic action due to the physical flow. In addition, measurement can be carried out in a state free of effects or artifacts attributable to dynamic action on particles to be detected in a sample solution (such as hybrids containing a first nucleic acid probe in the present invention).

[Configuration of Photometric Analysis Device for Scanning Molecule Counting Method]

As schematically exemplified in FIG. 1(A), a basic configuration of the scanning molecule counting method can be realized with a photometric analysis device comprising the combination of the optics of a confocal microscope able to carry out FCS or FIDA and the like and a photodetector. With reference to the same drawing, a photometric analysis device 101 is composed of optics 102 to 117 and a computer 118 for controlling operation of each component of the optics and acquiring and analyzing data. The optics of the photometric analysis device 101 are the same as the optics of an ordinary confocal microscope, and therein, laser light (Ex) that has been emitted from light sources 102 and propagated through a single-mode optic fiber 103 is radiated in the form of light emitted at a predetermined angle and a characteristic NA from the outlet end of the fiber, after which it is collimated into a parallel beam by a collimator 104, reflected by a dichroic mirror 105 and reflecting mirrors 106, 107, and made to enter an object lens 108. A sample container dispensed with one to several tens of microliters of a sample solution or a microplate 109 having wells 110 arranged therein is typically arranged above the object lens 108, and laser light emitted from the object lens 8 converges at a focal point in the sample container or the wells 110 resulting in the formation of a region of high fluorescence intensity (excitation region). Target particles, a luminescent probe that binds with the particles, and typically, molecules labeled with a luminescent label such as a fluorescent dye are dispersed or dissolved in the sample solution, and when particles that have bound or hybridized with the luminescent probe (or luminescent probe that has dissociated from a particle after having bound to that particle according to an experimental mode) enter the excitation region, the luminescent probe is excited and light is emitted during that time. The emitted light (Em) passes through the object lens 108 and the dichroic mirror 105, is reflected by a mirror 111, is concentrated by a condenser lens 112, passes through a pinhole 113, passes through a barrier filter 114 (here, only a component of the light of a specific wavelength band is selected), is led into a multi-mode optic fiber 115 where it reaches photodetectors 116, and after being converted to a chronological electrical signal, is input into the computer 118 where processing is carried out for optical analysis in a mode to be subsequently explained. Furthermore, as is known by a person with ordinary skill in the art, in the aforementioned configuration, the pinhole 113 is arranged at a location hybrid to the focal position of the object lens 108, and as a result thereof, only light emitted from an in-focus region, namely an excitation region, of laser light as schematically indicated in FIG. 1(B) passes through the pinhole 113, while light other than that of the excitation region is blocked. The in-focus region of laser light exemplified in FIG. 1(B) is normally a photodetection region in the present photometric analysis device having an effective volume of about 1 fL to 10 fL (and typically luminous intensity is in the form of a Gaussian distribution or Lorenzian distribution having the center of the region as the apex thereof The effective volume has a roughly elliptical shape having a plane in which luminescence intensity is $1/e^2$ as a boundary thereof), and is referred to as a confocal volume. In addition, in the scanning molecule counting method, since light from a hybrid of a single particle and luminescent probe or the light from a luminescent probe, such as faint light from one or a plurality of fluorescent dye molecules, is detected, photodetectors of extremely high sensitivity that can be used for photon counting may be used for the photodetectors 116. In addition, a stage repositioning device 117a is provided on a microscope stage (not shown) for moving the position of the microplate 109 in the horizontal direction in order to change the well 110 to be observed. Operation of the stage repositioning device 117a is controlled by the computer 118. According to this configuration, rapid measurement can be achieved in the case a plurality of specimens are present.

Moreover, in the optics of the aforementioned photometric analysis device, a mechanism is provided for scanning a sample solution according to a photodetection region by changing the light path of the optics, namely for moving the location of the in-focus region (namely, the photodetection region) in the sample solution. In an example of this mechanism for moving the location of the photodetection region as schematically exemplified in FIG. 1(C), a mirror deflector is employed that changes the orientation of the reflecting mirror 107. This mirror deflector 117 is similar to a galvanometer mirror device provided in an ordinary laser scanning microscope. In addition, the mirror deflector 117 is driven in coordination with detection of light by the photodetectors 116 under the control of the computer 118 so as to achieve a desired movement pattern for the location of the photodetection region. The movement locus of the location of the photodetection region is arbitrarily selected from a circular shape, elliptical shape, rectangular shape, straight line, curve or combination thereof (and various movement patterns can be selected in a program in the computer 118). Furthermore, although not shown in the drawings, the location of the photodetection region may be moved in the vertical direction by moving the object lens 108 up and down. As has been described above, if a configuration is employed in which the location of the photodetection region is moved by changing the light path of the optics instead of moving the sample solution, there is no substantial generation of mechanical vibrations or fluid dynamic action in the sample solution, the effects of dynamic action on the observation target can be eliminated, and stable measurement is achieved.

In the case a hybrid of a particle and luminescent probe or a luminescent probe emits light by multiphoton absorption, the aforementioned optics are used in the form of a multiphoton microscope. In that case, since light is emitted only at the in-focus region (photodetection region) of excitation light, the pinhole 113 may be eliminated. In addition, in the case a hybrid of a particle and luminescent probe or a luminescent probe emits light by a chemiluminescent or bioluminescent phenomenon without relying on excitation light, optics 102 to 105 for generating excitation light are omitted. In the case a hybrid of a particle and luminescent probe or a luminescent probe emits light phosphorescence or scattering, the aforementioned optics of a confocal microscope are used as is. Moreover, in the photometric analysis device 101, a plurality of excitation light sources 102 is provided as shown in the drawings, and the wavelength of excitation light can be suitably selected according to the wavelength of light that excites a hybrid of a particle and luminescent probe or a luminescent probe. Similarly, a plurality of photodetectors 106 is provided, and in the case a plurality of types of hybrids of particles and luminescent probes or luminescent probes having different wavelengths are contained in the sample, the light therefrom can be detected separately according to wavelength.

[Principle of Photometric Analysis Technology of Scanning Molecule Counting Method]

Photometric analysis technologies such as FIDA are superior to conventional biochemical analysis technologies in that the amount of sample required is extremely small and that testing can be performed rapidly. However, in the case of photometric analysis technologies such as FIDA, since the concentration and properties of target particles are determined based on fluctuations in fluorescence intensity in accordance with the principle employed by these technologies, in order to obtain accurate measurement results, the concentration or number density of the target particles in a sample solution must be of a level at which about one of the target particles is present in a photodetection region (confocal volume) CV at all times during measurement of fluorescence intensity, and significant luminous intensity (photon count) is required to always be detected during the measurement time. In the case the concentration or number density of target particles is lower that that level, such as in the case of a level at which the target particles only rarely enter the photodetection region CV, significant luminous intensity (photon count) only appears during a portion of the measurement time, thereby making it difficult to accurately determine fluctuations in luminous intensity. In addition, in the case the concentration of the target particles is considerably lower than the level at which about one target particle is present in the photodetection region during measurement, determination of fluctuations in luminous intensity are subjected to background effects, and measurement time is prolonged in order to obtain an amount of significant luminous intensity data sufficient for calculation. In contrast, in the scanning molecule counting method, properties such as the number density or concentration of target particles can be detected even in cases in which the concentration of the target particles is lower than the level required by FIDA and other photometric analysis technologies.

Figure 2:
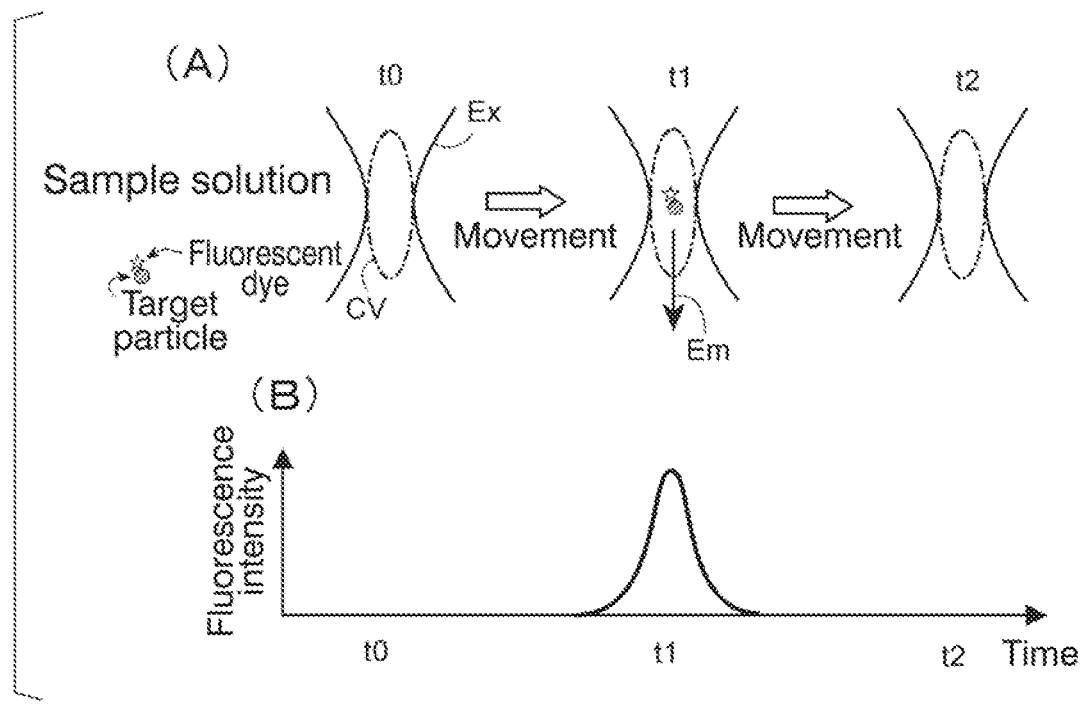
FIGS. 2(A) and 2(B) are a schematic diagram for explaining the principle of photodetection by photometric analysis technology for a scanning molecule counting method, and a schematic diagram of time-based changes in luminous intensity as measured by photometric analysis technology for a scanning molecule counting method, respectively.

In the photometric analysis technology employed by the scanning molecule counting method, photodetection schematically depicted in FIG. 2 is performed. In this photodetection, the light path is varied by driving a mechanism for moving the location of the photodetection region (mirror deflector 117). Then, the photodetection is performed while moving the location of the photodetection region CV in the sample solution, namely while scanning the sample solution with the photodetection region CV. In this way, during the time the photodetection region CV is moving in the manner of FIG. 2(A), for example (time t0 to time t2 in the drawing), significant luminous intensity (Em) is detected as depicted in FIG. 2(B) when it passes through a region where a single particle (a fluorescent dye is bound to the particle as a luminescent probe in the drawing) is present (time t1). Thus, by individually detecting significant luminous intensity as exemplified in FIG. 2(B) that appears during the time movement of the location of the photodetection region CV and photodetection are carried out as previously described, particles bound with the luminescent probe are detected individually, and by counting the number of those particles, the number of particles present in the measured region or information relating to their concentration or number density can be acquired. In the principle of this photometric analysis technology employed by the scanning molecule counting method, since statistical arithmetic processing is not carried out in the manner of determination of fluctuations in fluorescence intensity, but rather particles are detected one at a time, it can be understood that information relating to particle concentration or number density can be acquired even in sample solutions in which the concentration of particles to be observed is sufficiently low so as to prevent analysis with adequate accuracy by a method such as FIDA.

In addition, according to a method for counting particles in a sample solution by individually detecting those particles as in the scanning molecule counting method, particles can be measured at a lower concentration than in the case of measuring the concentration of fluorescent-labeled particles based on fluorescence intensity measured with a fluorescence spectrophotometer or plate reader. In the case of measuring the concentration of fluorescence-labeled particles with a fluorescence spectrophotometer or plate reader, fluorescence intensity is normally assumed to be proportional to the concentration of the fluorescence-labeled particles. However, if the concentration of the fluorescence-labeled particles becomes sufficiently low, the amount of noise signals relative to the amount of signals generated by light emitted from the fluorescence-labeled particles increases (resulting in a poor S/N ratio), the proportional relationship between the concentration of fluorescence-labeled particles and optical signal volume is disrupted, and accuracy of the determined concentration values becomes poor. On the other hand, in the scanning molecule counting method, fluorescence intensity can be detected accurately even if the sample concentration is lower than the case in which the concentration is detected based on the assumption that the fluorescent intensity is proportional to the concentration of fluorescent-labeled particles, since the noise signals are removed from the detected results and the concentration is calculated by counting the signals corresponding to the individual particles in detecting the signals corresponding to the individual particles from the detected optical signals.

Moreover, in the case a plurality of luminescent probes are bound to a single target particle, according to a method for counting particles in a sample solution by individually detecting those particles as in the scanning molecule counting method, the accuracy of measuring particle concentration at high particle concentrations also improves more than the conventional method for determining concentration based on the assumption that fluorescence intensity is proportional to the concentration of fluorescence-labeled particles. In the case a plurality of luminescent probes are bound to a single target particle, when the concentration of target particles increases when a certain amount of luminescent probe is added to a sample solution, the number of fluorescent probes bound to the particles decreases relative thereto. In that case, since fluorescence intensity per target particle decreases, the proportional relationship between the concentration of fluorescence-labeled particles and the amount of light is disrupted, and accuracy of the determined concentration values becomes poor. On the other hand, in the scanning molecule counting method, since concentration is calculated from the number of particles while only being minimally affected by decreases in fluorescence intensity per particle in detecting signals corresponding to individual particles from the detected optical signals, fluorescence intensity can be detected accurately even if the sample concentration is lower than the case in which the concentration is detected based on the assumption that the fluorescent intensity is proportional to the concentration of fluorescent-labeled particles.

[Measurement of Luminous Intensity of Sample Solution by Scanning Molecule Counting Method]

Measurement of luminous intensity in optical analyses using the scanning molecule counting method is carried out in the same manner as the process for measuring luminous intensity in FCS or FIDA with the exception of moving the location of the photodetection region in the sample solution (scanning the sample solution) by driving the mirror defector 117 during measurement. During this operation processing, typically when a user enters instructions for initiating measurement to the computer 118 after having injected a sample solution into the wells 110 of the microplate 109 and placing on a microscope stage, the computer 118 initiates radiation of excitation light in a photodetection region in the sample solution and begins measuring luminous intensity in accordance with a program stored in a storage device (not shown) (consisting of a procedure for changing the light path so as to move the location of the photodetection region in the sample solution and a procedure for detecting light emitted from the photodetection region during movement of the location of the photodetection region). During this measurement, the mirror deflector 117 drives the mirror 107 (galvanometric mirror) under the control of a processing operation in accordance with the program of the computer 118, movement of the location of the photodetection region in the wells 110 is carried out, and simultaneous thereto, the photodetector 116 converts successively detected light to electrical signals and transmits the electrical signals to the computer 118, and in the computer 118, chronological luminous intensity data is generated from the transmitted optical signals in an arbitrary mode. Furthermore, since the photodetector 116 is typically an extremely sensitive photodetector capable of detecting the arrival of a single photon, detection of light is in the form of photon counting carried out in a mode by which the number of photons is counted that successively arrive at the photodetector per predetermined unit time over a predetermined time period (BIN TIME), such as by counting the number of photons every 10 microseconds, and chronological luminous intensity data may be chronological photon count data.

Movement speed of the location of the photodetection region during measurement of luminous intensity is an arbitrary speed such as a predetermined speed set experimentally or so as to coincide with the objective of the analysis. In the case of acquiring information relating to number density or concentration based on the number of target particles observed, the movement of the location of the photodetection region is carried out in a mode by which movement distance is determined since a certain size or volume is required of the region that passes through the photodetection region. Furthermore, since the existence of a proportional relationship between elapsed time during measurement and movement distance of the location of the photodetection region facilitates interpretation of measurement results, it is preferable that the movement speed basically be a constant speed, although not limited thereto.

Figure 3:
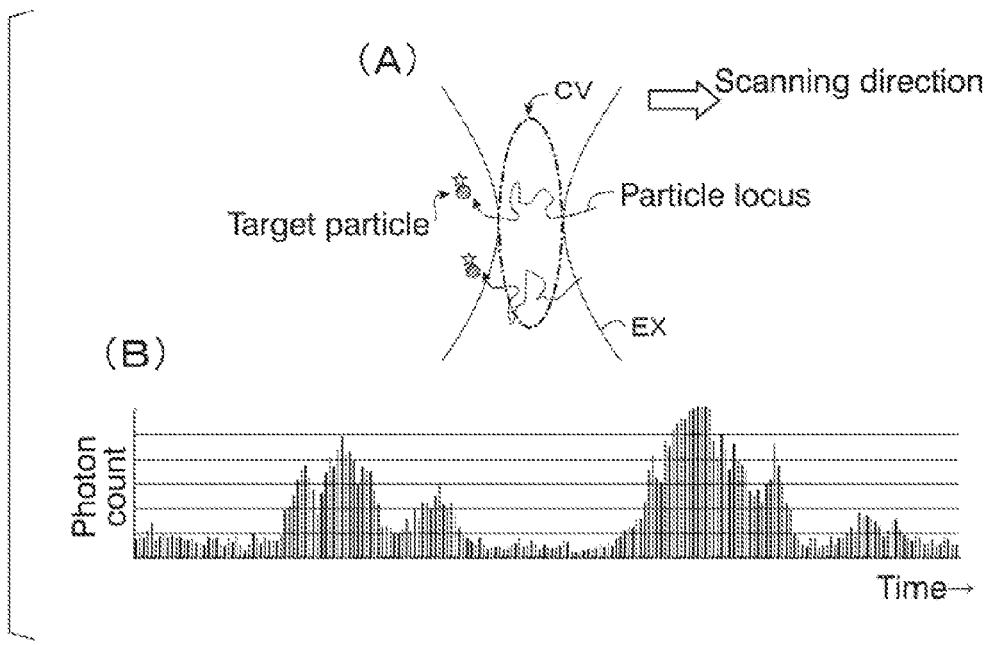
FIGS. 3(A) and 3(B) are a drawing of a model in the case target particles traverse a photodetection region while demonstrating Brownian motion, and a drawing showing an example of time-based changes in photon count (luminous intensity) in the case shown in FIG. 3(A), respectively.
Figure 4:
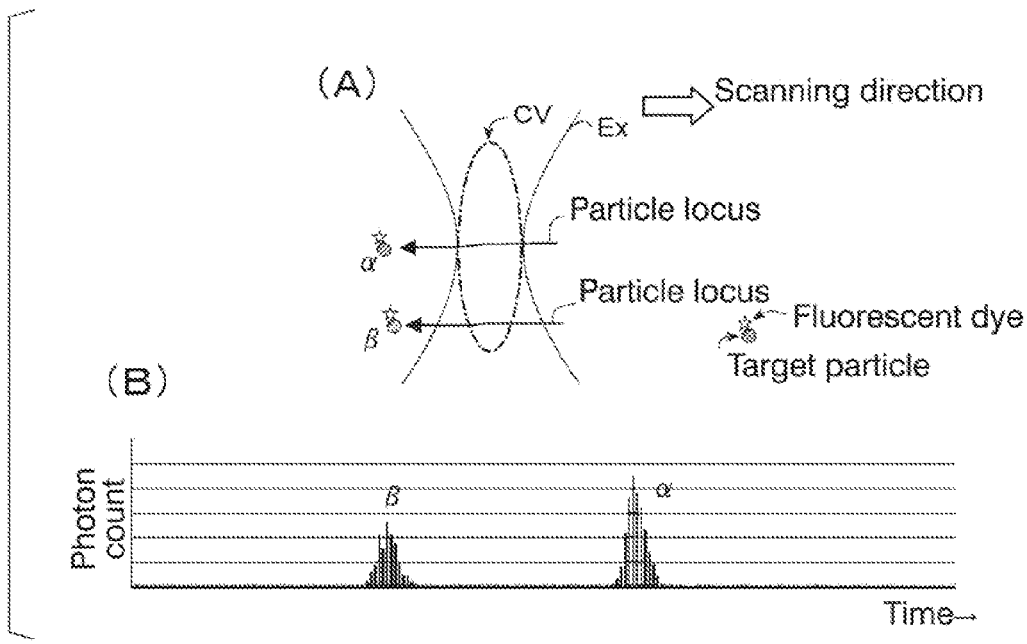
FIGS. 4(A) and 4(B) are a drawing of a model in the case target particles traverse a photodetection region as a result of moving the location of the photodetection region in a sample solution at a speed faster than the speed of spreading diffusion of the target particles, and a drawing showing an example of time-based changes in photon count (luminous intensity) in the case shown in FIG. 4(A), respectively.

However, with respect to movement speed of the location of the photodetection region, in order to quantitatively and accurately carry out individual detection of target particles from measured chronological luminous intensity data or count the number of target particles, the movement speed may be set to a value that is faster than the random motion of the target particles (and more precisely, hybrids of the particles and a luminescent probe or a luminescent probe that is dissociated and released after binding with the particles), or in other words, faster than the speed of movement attributable to Brownian motion. Since particles measured with the photometric analysis technology employed by the scanning molecule counting method are particles that are dispersed or dissolved in a solution and move freely in random motion, their locations move over time due to Brownian motion. Thus, in the case the movement speed of the location of the photodetection region is slower than the movement of particles attributable to Brownian motion, since the particles move randomly in the region as schematically depicted in FIG. 3(A), luminous intensity changes randomly in the manner of FIG. 3(B) (and excitation luminous intensity of the photodetection region decreases moving to the outside with the center of the region serving as the peak thereof as was previously mentioned), thereby making it difficult to specify changes in significant luminous intensity corresponding to individual target particles. Therefore, the movement speed of the location of the photodetection region may be set to be faster than the average movement speed of the particles attributable to Brownian motion (spreading diffusion speed) so that the particles traverse the photodetection region roughly in a straight line as depicted in FIG. 4(A), and as a result thereof, a profile of changes in luminous intensity corresponding to individual particles in chronological luminous intensity data becomes roughly uniform as exemplified in FIG. 4(B) (the profile of changes in luminous intensity become roughly similar to the distribution of excitation luminous intensity in the case the particles pass through the photodetection region in roughly a straight line), and the correlation between individual target particles and luminous intensity can be easily specified.

More specifically, since a time $\Delta t$ required by a target particle having a diffusion coefficient D (and more precisely, a hybrid of the particle and a luminescent probe or a luminescent probe that has dissociated and released after binding with a particle) when passing through a photodetection region (confocal volume) having a radius Wo due to Brownian movement is based on a function of mean square displacement represented by the equation (1) shown below:

$$(2Wo)^2 = 6D \cdot \Delta t \quad (1)$$

from which is derived the following equation:

$$\Delta t = (2Wo)^2/6D \quad (2)$$

a speed (spreading diffusion speed) Vdif at which a target particle moves due to Brownian motion can be approximately represented by the equation indicated below.

$$Vdif = 2Wo/\Delta t = 3D/Wo \quad (3)$$

Therefore, the movement speed of the location of the photodetection region is set to a value that is sufficiently faster than Vdif by referring to this value of Vdif. For example, in the case the diffusion coefficient D of a target particle is predicted to be about $2.0 \times 10^{-10}$ m$^2$/s and Wo is taken to be about 0.62 µm, in order to obtain a value of Vdif of $1.0 \times 10^{-3}$ m/s, the movement speed of the location of the photodetection region is set to a value of 15 mm/s equal to roughly ten times that value. Furthermore, in the case the diffusion coefficient of a target particle is unknown, the preferable movement speed of the location of the photodetection region is determined by finding those conditions under which the profile of changes in luminous intensity becomes a predicted profile (and typically, a profile roughly similar to the excitation luminous intensity distribution) by setting various movement speeds for the location of the photodetection region.

[Analysis of Luminous Intensity by Scanning Molecule Counting Method]

When chronological luminous intensity data of a sample solution is obtained according to the processing described above, analysis of luminous intensity is carried out in the computer 118 in the manner described below by processing in accordance with a program stored in a storage device.

(1) Detection of Single Target Particle

Figure 6:
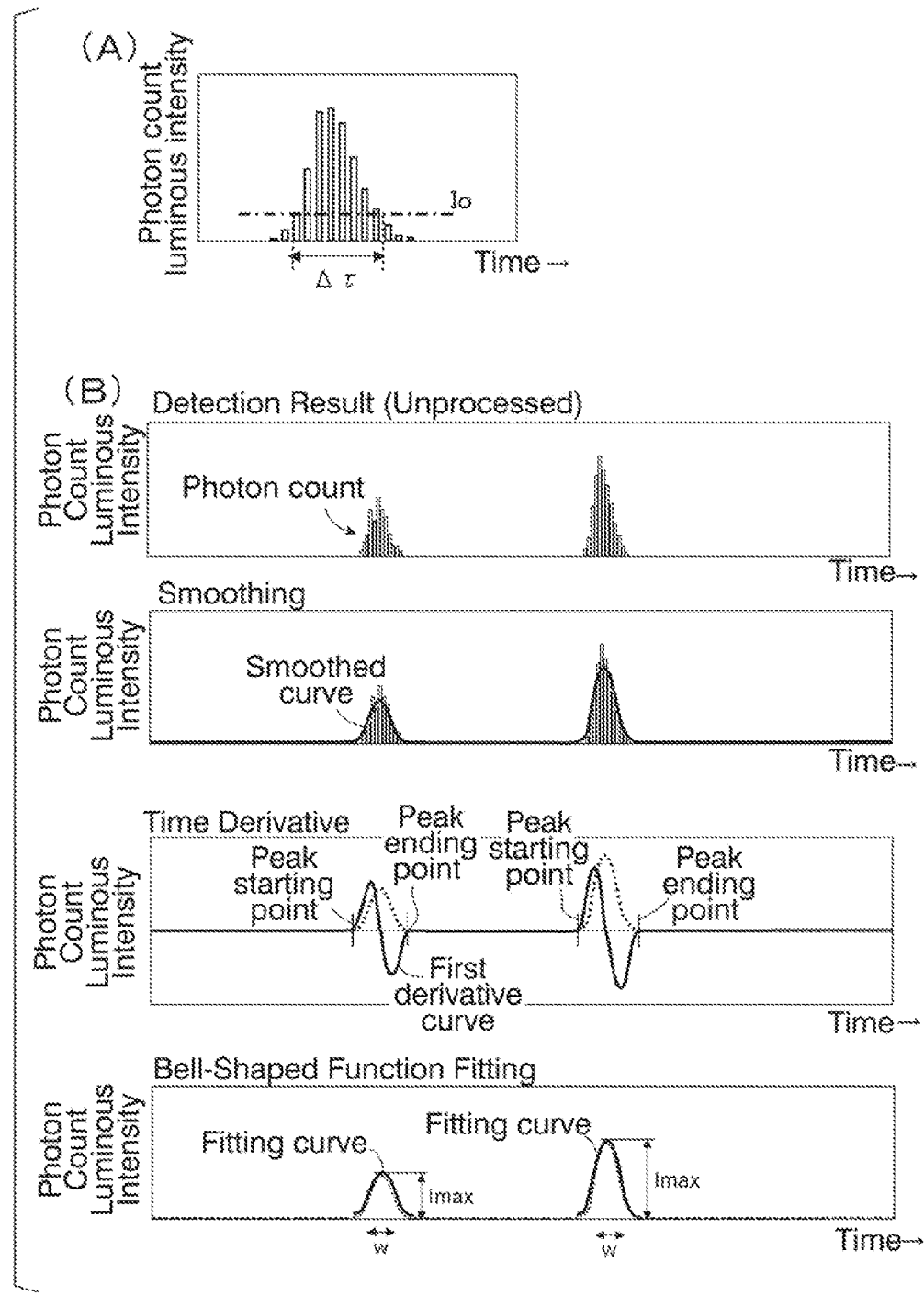
FIG. 6 a drawing for explaining an example of a signal processing step for detection signals in a processing procedure for counting particles based on time-based changes in photon count (luminous intensity) measured according to a scanning molecule counting method.

In chronological luminous intensity data, in the case the locus when a single target particle passes through the photodetection region is roughly a straight line as shown in FIG. 4(A), the change in luminous intensity corresponding to that particle has a profile that reflects the distribution of luminous intensity of the photodetection region (determined by the optics) as schematically depicted in FIG. 6(A). Therefore, in one technique for detecting the target particle, a threshold Io is set for luminous intensity, and when a duration $\Delta \tau$ during which luminous intensity that exceeds that threshold persists is within a predetermined range, the prolife of that luminous intensity is judged to correspond to the passage of a single particle through the photodetection region, and a single target particle is detected. When the threshold Io for luminous intensity and the predetermined range for duration $\Delta \tau$ are determined based on a profile presumed to be the intensity of light emitted from a hybrid of a target particle and luminescent probe that moves relative to the photodetection region at a predetermined speed (or a luminescent probe that has dissociated and released after binding with the particle), the specific values are arbitrarily set experimentally, or are determined selectively according to the properties of the hybrid of the target particle and luminescent probe (or luminescent probe that dissociated and released after binding with the particle).

In addition, as an example of another technique used to detect a target particle, when the distribution of luminous intensity of a photodetection region is assumed to have a Gaussian distribution as represented by:

$$I = A \cdot \exp(-2t^2/a^2) \quad (4)$$

and intensity A and width a, as calculated by fitting equation (4) to a profile of significant luminous intensity (profile which can clearly be judged to not constitute background noise), are within predetermined ranges, the prolife of that luminous intensity is judged to correspond to a single target particle having passed through the photodetection region, and a single target particle is detected (when intensity A and width a are outside the predetermined ranges, the particle is treated as noise or artifact and is ignored during analysis).

(ii) Counting Target Particles

Target particles are counted using an arbitrary technique by counting the number of particles detected by a technique used to detect target particles as described above. However, in the case of a large number of particles, the particles are counted by carrying out the processing exemplified in FIGS. 5 and 6B, for example.

Figure 5:
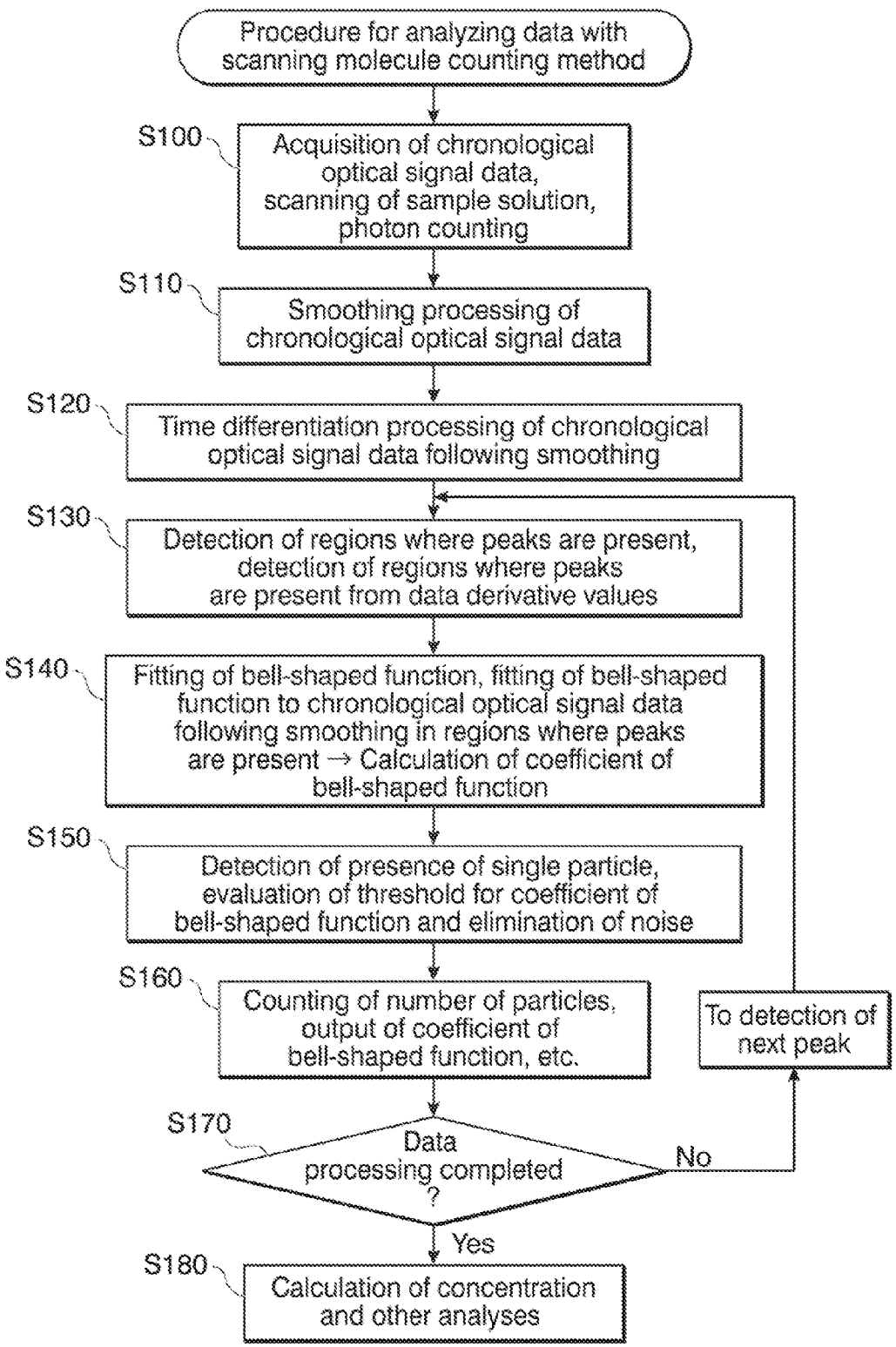
FIG. 5 is a drawing representing the processing procedure for counting particles based on time-based changes in photon count (luminous intensity) measured by a scanning molecule counting method in the form of a flow chart.

With reference to FIGS. 5 and 6B, photon counting of the target particles is explained. In one example of a technique used to count particles using chronological luminous intensity (photon count) data, after measuring luminous intensity as explained above, or in other words, after having acquired chronological optical signal data (photon count data) by scanning a sample solution with a photodetection region and counting the number of photons (Step 100), smoothing (Step 110, second graph from top in FIG. 6(B) indicated by "Smoothing") is carried out on the chronological optical signal data (uppermost graph in FIG. 6(B) indicated by "Detection Results (unprocessed)"). Since light emitted by hybrids of the particles and luminescent probe or light emitted by the luminescent probe is emitted probabilistically, and missing data values can occur for extremely small amounts of time, the loss of data values as described above can be ignored by carrying out this smoothing processing. Smoothing processing is carried out using, for example, the moving average method. Furthermore, parameters used when carrying out smoothing processing with the moving average method, such as the number of data points that are averaged at one time or the number of times movement is averaged, are suitably set corresponding to the movement speed (scanning speed) of the location of the photodetection region when acquiring optical signal data and bin time.

Next, in chronological optical signal data obtained following smoothing processing, a first derivative is calculated for the time of chronological optical signal data after smoothing processing in order to detect the time region where a significant signal is present (peak region) (Step 120). Since the value of the time derivative of chronological optical signal data changes considerably at times when the signal value changes as exemplified in the second graph from the bottom of FIG. 6(B) indicated by "Time Derivative", the starting points and ending points of significant signals (peak signals) can be advantageously determined by referring to the value of the time derivative.

Figure 7:
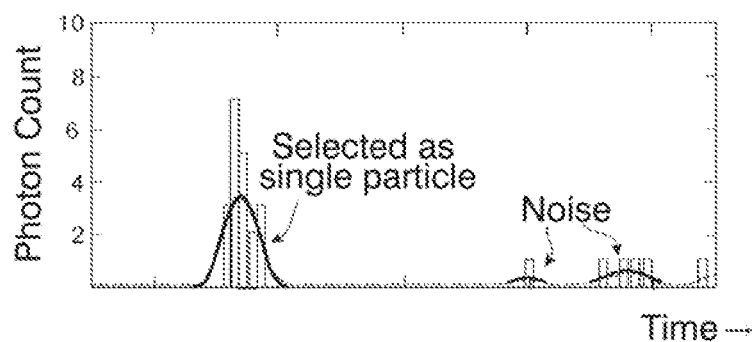
FIG. 7 shows an example of measuring photon count data measured according to a scanning molecule counting method (bar graph), a curve obtained by smoothing the data (dotted line), and a Gaussian function fit to the regions where peaks are present. In the drawing, the signal indicated with "noise" is ignored since it is a signal attributable to noise or artifact.

Subsequently, in the chronological optical signal data, significant signals (peak signals) are detected successively, and a judgment is made as to whether or not a detected peak signal is a signal corresponding to a target particle. More specifically, the starting point and ending point of a single peak signal are first searched for and determined by successively referring to time derivative values in chronological time derivative value data of the chronological optical signal data to specify a peak region (Step 130). When a single peak region has been specified, fitting based on a bell-shaped function is carried out on the smoothed chronological optical data in that peak region (bottom graph in FIG. 6(B) indicated by "Bell-Shaped Function Fitting"), and parameters such as the peak intensity Imax of the bell-shaped function, the peak width (full width half maximum) w and the correlation coefficient (of the least squares method) used during fitting are calculated (Step 140). Furthermore, although the bell-shaped function that is fit is typically a Gaussian function, it may also be a Lorenzian function. A judgment is then made as to whether or not the calculated bell-shaped function parameters are within the presumed range of parameters of a bell-shaped profile depicted by optical signals detected when a hybrid or a single particle and luminescent probe or a luminescent probe has passed through the photodetection region, or in other words, whether or not peak intensity, peak width and correlation coefficient are respectively within their predetermined ranges (Step 150). Thus, as shown on the left side of the graph of FIG. 7, a signal, for which calculated bell-shaped function parameters have been judged to be within the presumed range for an optical signal corresponding to a hybrid of a single particle and luminescent probe or a luminescent probe, is judged to be a signal corresponding to a single target particle, and as a result thereof, a single target particle is detected and counted as a single particle (and the particle count is increased by 1, Step 160). On the other hand, as shown on the right side of the graph of FIG. 7, a peak signal for which calculated bell-shaped function parameters are not within the presumed ranges is treated as noise and ignored.

The search and judgments carried out on peak signals in the processing of the aforementioned Steps 130 to 160 are carried out repeatedly over the entire range of chronological optical signal data, and each time a single target particle is detected, the target particle is counted as a particle. When the search for peak signals over the entire range of chronological optical signal data has been completed (Step 170), the particle count value obtained thus far is taken to be the number of target particles detected in the chronological optical signal data (Step 180, see the following paragraph for detail).

(iii) Determination of Number Density or Concentration of Target Particles

When target particles have been counted, the number density or concentration of the target particles is determined by using the total volume of the region through which the target particles passed during acquisition of chronological optical signal data. However, since the effective volume of the photodetection region varies depending on the wavelength of excitation light or detection light, numerical aperture of the lens, and the state of adjustment of the optics, it is generally difficult to estimate total volume from design values, and therefore, determining the total value of the region of the photodetection region that target particles have passed through is not easy. Therefore, measurement of luminous intensity and detection and counting of particles as previously explained are typically carried out on a solution having a known concentration of particles (reference solution) under the same conditions as measurement of a standard solution to be tested, and then total volume of the region of the photodetection region through which particles have passed, namely the relationship between the number and concentration of target particles detected, is determined from the number of detected particles and the concentration of particles in the reference solution. The particles in the reference solution may be a luminescent label having wavelength characteristics similar to those of hybrids of the particles and luminescent probe formed by the target particles (or luminescent probe that has been released after binding to the target particles). More specifically, if the number of detected particles is assumed to be N for a reference solution having a particle concentration C, then the total volume Vt of a region of the photodetection region through which the particles have passed is given by the following equation (5) shown below:

$$Vt = N/C \tag{5}$$

In addition, solutions having multiple different concentrations are prepared, measurement is carried out on each solution, and the average value of the calculated values of Vt is used as the total volume Vt of the region of the photodetection region through which the particles have passed. If Vt is given, then the number density c of particles in a sample solution for which the result of counting the number of particles is n is given by the following equation (6) shown below:

$$c = n/Vt \qquad (6)$$

Furthermore, the volume of the photodetection region and the total volume of the region of the photodetection region through which particles have passed are not dependent upon the aforementioned equations, but rather may also be given by using an arbitrary method such as FCS or FIDA. In addition, in the photometric analysis device of the present embodiment, information on the relationship between concentration C and the number of particles N (Equation (5)) for various standard particles with respect to presumed movement patterns in the photodetection region may be stored in advance in a storage device of the computer 18, and a device user can suitably use the stored relationship information when carrying out photometric analyses.

[Method for Identifying Polymorphism of Nucleic Acid Molecules]

The method for identifying polymorphism of nucleic acid molecules of the present invention is a method for identifying polymorphism of target nucleic acid molecules that uses a nucleic acid probe that specifically binds with a nucleic acid molecule of a specific type (first type) in a polymorphic sequence. In the method of identifying polymorphism of nucleic acid molecule of the present invention, the nucleic acid probe and the nucleic acid molecules of the target particles are hybridized, and the type of the target nucleic acid is identified based on the amount of the hybrids formed. Moreover, in the present invention, detection of the hybrid is measured according to the aforementioned scanning molecule counting method. Since the scanning molecule counting method is a measurement method that is able to measure particles having fluorescence one at a time in a state in which the particles are dispersed, nucleic acid molecules can be measured even at comparatively low concentrations on the pM order or lower. Consequently, according to the method for identifying polymorphism of nucleic acid molecules of the present invention, formed hybrids can be counted with high sensitivity even in cases in which the concentration of target nucleic acid molecules in a sample solution is extremely low.

In the present invention and description of the present application, "polymorphic sequence" refers to a base sequence for which two or more mutually similar base sequences are present, and a nucleic acid molecule having a polymorphic sequence is referred to as a polymorphic nucleic acid. Here, "similar base sequence" refers to one to several nucleic acid bases among 10 to 20 nucleic acid bases, for example, differing due to substitution, deletion, insertion or duplication. In addition, "identifying polymorphism" refers to distinguishing between a nucleic acid molecule having a specific type of base sequence in a polymorphic sequence and a nucleic acid molecule having a type of base sequence other than the specific type of base sequence in that polymorphic sequence.

The target polymorphic sequence in the method for identifying polymorphism of nucleic acid molecules of the present invention may be a base sequence in a gene such as a single nucleotide polymorphism (SNP) and an artificial base sequence. In the present invention, a polymorphic site of a congenital polymorphism in the form of a genetic polymorphism or a mutated site of an acquired polymorphism in the form of a somatic mutation may be identified. An example of a somatic mutation is a mutation of the K-ras gene.

In the present invention, a "nucleic acid probe specifically binding to a single-stranded nucleic acid molecule having a specific type in a polymorphic sequence" refers to the nucleic acid probe preferentially hybridizing with the single-stranded nucleic acid molecule of a specific type rather than a single-stranded nucleic acid molecule of a type other than the specific type among single-stranded nucleic acid molecules having the polymorphic sequence. Consequently, the nucleic acid probes may have a base sequence completely complementary to a specific type of base sequence, or may have a base sequence having mismatches other than at a polymorphic site where the base sequence differs between polymorphic sequences.

In the present invention, a first nucleic acid probe that hybridized with a specific type (a first type) of a single-stranded nucleic acid molecule having a first type of base sequence in a polymorphic sequence (to be referred to as the "first nucleic acid probe") is used. Whether the polymorphic sequence in the nucleic acid molecule is identical to the first type or not can be determined by hybridizing the target nucleic acids and the first nucleic acid probe and by detecting the hybrid formed. For example, whether the target nucleic acid molecule is a mutation type or a wild type can be determined by setting the first type to be the mutation type in identification of a gene polymorphism known to have two types of the wild type and the mutation type. If the target nucleic acid is the mutation type, the hybrid including the first nucleic acid probe is detected in the sample solution.

The nucleotide probe used in the present invention such as the first nucleic acid probe or the like may be oligonucleotides composed of DNA, oligonucleotides composed of RNA, chimeric oligonucleotides composed of DNA and RNA, or that containing all or a portion of a nucleic acid analogue capable of forming nucleotide strands and base pairs in the manner of naturally-occurring nucleic acid bases. Examples of nucleic acid analogues include those in which side chains and the like of naturally-occurring nucleotides (nucleotides present in nature) like DNA or RNA are modified with an amino group or other functional group, and those labeled with proteins or low molecular weight compounds and the like. Specific examples include bridged nucleic acids (BNA), nucleotides in which an oxygen atom at the 4' position of a naturally-occurring nucleotide is substituted with a sulfur atom, nucleotides in which a hydroxyl group at the 2' position of a naturally-occurring nucleotide is substituted with a methoxy group, hexitol nucleic acids (HNA) and peptide nucleic acids (PNA). In addition, the target nucleic acid may be DNA or RNA, or may be artificially amplified in the manner of cDNA.

In the present invention, the hybrid, which is formed by the nucleic acid probe and the other single-stranded nucleic acid molecule, and the nucleic acid probe, which is not forming a hybrid, can be detected separately by creating a difference in fluorescence intensity between a state in which the nucleic acid probe is present alone and a state in which the hybrid is formed with the other single-stranded nucleic acid molecule.

For example, the hybrid including the nucleic acid probe can be detected separately from the nucleic acid probe present alone by configuring a nucleic acid probe not having a double-stranded structure when it presents alone to be the first nucleic acid probe and using a fluorescent double-stranded nucleic acid-binding substance that specifically binds to double-stranded structures. In this case, the nucleic acid probe present alone is not labeled with the fluorescent substance. Therefore, it does not emit fluorescence. Contrary to that, since the fluorescent double-stranded nucleic acid-binding substance binds with the hybrid including the nucleic acid probe, fluorescence emitted from the fluorescent double-stranded nucleic acid-binding substance can be detected from the hybrid.

In addition, the hybrid including the nucleic acid probe can be detected by distinguishing the hybrid including the nucleic acid probe from the nucleic acid probe present alone by using a nucleic acid probe, which is labeled with a fluorescent substance causing the fluorescence energy transfer (FRET) with a fluorescent double-stranded nucleic acid-binding substance. Namely, one of either the fluorescent double-stranded nucleic acid binding substance or the fluorescent substance used to label the nucleic acid probe serves as an energy donor during FRET while the other serves as an energy acceptor. Fluorescence emitted from the fluorescent substance used to label the nucleic acid probe is detected from the first nucleic acid probe or the like that is present alone. In contrast, since fluorescence emitted by FRET can be detected due to binding of the fluorescent double-stranded nucleic acid-binding substance to the hybrid, the hybrid can be detected separately from the nucleic acid probe present alone.

Examples of fluorescent double-stranded nucleic acid binding substances that specifically bind to a double-stranded structure include a fluorescent intercalators and groove binders bound with a fluorescent substance. Furthermore, in the case the amount of fluorescent intercalator that penetrates between the base pairs of a hybrid is excessively large, the background level when detecting fluorescence emitted by FRET becomes excessively high, thereby resulting in the risk of having an effect on detection accuracy. Consequently, the first nucleic acid probe or the like may be designed so that the region where a double-strand is formed in a hybrid is 400 bp or less.

In addition, a molecular beacon probe can be used for the nucleic acid probe. The molecular beacon probe is an oligonucleotide that forms an intramolecular structure when it is in the state of a single-stranded nucleic acid molecule. In the molecular beacon probe, a fluorescent substance serving as an energy donor in FRET and a substance serving as an energy acceptor (fluorescent substance or quenching substance) are bound so that FRET occurs in the state of a single-stranded nucleic acid molecule but does not occur in the state of a hybrid formed by hybridizing with another single-stranded nucleic acid molecule. While the fluorescence, which is emitted from the fluorescent substance serving as an energy donor, is detected from the nucleic acid probe forming the hybrid, fluorescence emitted from the fluorescent substance serving as an energy donor is not detected or is diminished from the nucleic acid probe when presents alone. Therefore, by detecting fluorescence emitted from the fluorescent substance serving as an energy donor, the hybrid of the nucleic acid probe can be detected separately from a nucleic acid probe present alone.

An example of the molecular beacon probe used for the first nucleic acid probe is an oligonucleotide that has a base sequence capable hybridizing with a specific type of polymorphic sequence, and has mutually complementary base sequences in the region on the 3'-terminal side and the region on the 5'-terminal side. In the present invention, a fluorescent substance serving as an energy donor or a substance serving as an energy acceptor is bound to the 3'-terminal side, the other remaining substance is bound to the 5'-terminal side, the molecular beacon probe has mutually complementary base sequences in the region on the 3'-terminal side and 5'-terminal side, and may form an intramolecular structure (so-called stem-loop structure) as a result of these base sequences forming base pairs. The mutually complementary regions of the molecular beacon that form intramolecular base pairs are present so as to surround the region having a base sequence complementary to the target nucleic acid molecule, and the region on the 3'-terminal side and the region on the 5'-terminal side may be regions that respectively contain the 3'-terminal or the 5'-terminal or regions that do not contain these terminals. In addition, in terms of the number of bases and base sequences of the regions that form base pairs, what is needed is that the stability of the formed based pairs is lower than the stability of the hybrid with the target nucleic acid molecule, and the internal base paring is formed under the measurement condition.

The kind of the fluorescent substance is not particularly limited as long as the substance emits fluorescence by irradiating light with a specific wave length. Therefore, it can be appropriately chosen from the fluorescent dyes used in FCS, FIDA, or the like. Also, labeling of the nucleic acid probe with the fluorescent substance can be performed by the conventional methods.

Alternatively, the hybrid including the first nucleic acid probe can be detected separately from the first nucleic acid present alone by using a nucleic acid probe, which is designed to hybridize specifically with the single-stranded nucleic acid having the first type of the base sequence adjacently to the first nucleic acid probe. In this case, the first nucleic acid probe and the adjacently hybridizing nucleic acid probes are mutually adjacent and hybridize with the single-stranded nucleic acid molecule having a first type of base sequence. Therefore, in a hybrid composed of these three members, FRET occurs. Consequently, a hybrid containing the first nucleic acid probe can be detected by detecting fluorescence emitted by that FRET.

The method for identifying polymorphism of nucleic acid molecules of the present invention specifically has the steps indicated below.

(a) preparing a sample solution comprising a first nucleic acid probe, which specifically hybridizes with a single-stranded nucleic acid molecule including a first type of base sequence in a polymorphic sequence, and a target nucleic acid molecule;

(b) forming a hybrid of the nucleic acid molecules in the sample solution prepared in (a);

(c) calculating a number of molecules of the hybrid including the first nucleic acid probe in the sample solution prepared in (a) after carrying out (b); and (d) identifying polymorphism of the target nucleic acid molecule based on a result of (c).

First, in (a), a sample solution is prepared that contains a first nucleic acid probe and a target nucleic acid molecule. More specifically, the first nucleic acid probe and the target nucleic acid molecule are added to a suitable solvent to prepare a sample solution. There are no particular limitations on the solvent provided it is a solvent that does not impair formation of the hybrid by the first nucleic acid probe or detection of the hybrid with the scanning molecule counting method, and can be used by suitably selecting from among buffers commonly used in that technical field. Examples of such buffers include phosphate buffers such as phosphate buffered saline (PBS, pH 7.4) and Tris buffer.

In a case where the fluorescent double-stranded nucleic acid-binding substance, which specifically binds with double-stranded structures, or a nucleic acid probe other than the first nucleic acid probe are used for detecting the hybrid including the first nucleic acid probe, the fluorescent double-stranded nucleic acid-binding substance or the nucleic acid probe other than the first nucleic acid probe is added to the sample solution as the first nucleic acid probe or the like.

Next, nucleic acid molecules in the sample solution prepared in (a) are hybridized in (b). In the case the nucleic acid molecules in the sample solution are double-stranded nucleic acid molecules, they may be denatured prior to conjugation.

In the present invention, denaturing a nucleic acid molecule refers to dissociating base pairs. For example, this refers to dissociating base pairs formed by mutually complementary base sequences in the single-stranded nucleic acid molecule, or denaturing a double-stranded nucleic acid molecule to a single-stranded nucleic acid molecule. Furthermore, in the case a nucleic acid probe is an oligonucleotide containing a nucleic acid analogue such as PNA, even if the nucleic acid molecule was a double-stranded nucleic acid molecule, there are cases in which a hybrid containing that nucleic acid probe can be formed without carrying out special denaturation treatment.

In the present invention, denaturation by high-temperature treatment (heat denaturation) or denaturation by low salt concentration treatment may be carried out since there is comparatively little effect on fluorescent substances. Heat denaturation is particularly preferable since the procedure is simple. More specifically, heat denaturation can be carried out by denaturing nucleic acid molecules in the sample solution by treating at a high temperature. In general, although denaturation can be carried out by heating at 90° C. in the case of DNA or at 70° C. in the case of RNA and holding at that temperature for several seconds to two minutes, the temperature at which denaturation is carried out varies infinitely depending on such factors as the base length of the target nucleic acid molecule, and there are no particular limitations on this temperature provided it allows denaturation to be carried out. On the other hand, denaturation by low salt concentration treatment can be carried out by adjusting the salt concentration of the sample solution to be sufficiently low by diluting with purified water and the like.

After denaturing as necessary, the nucleic acid molecules in the sample solution are hybridized. In the case of having carried out heat denaturation, nucleic acid molecules in the sample solution can be suitably hybridized by lowering the temperature of the sample solution to a temperature that allows the first nucleic acid probe to specifically hybridize with a single-stranded nucleic acid molecule having a first type of base sequence. In addition, in the case of having carried out denaturation by low salt concentration treatment, nucleic acid molecules in the sample solution can be suitably hybridized by raising the salt concentration of the sample solution to a concentration that allows the first nucleic acid probe to specifically hybridize with a single-stranded nucleic acid molecule having a first type of base sequence.

Furthermore, the temperature at which the first nucleic acid probe is able to specifically hybridize with a single-stranded nucleic acid molecule having a first type of base sequence can be determined from a melting curve of a hybrid composed of the nucleic acid molecule having a polymorphic sequence and a nucleic acid probe. A melting curve can be determined by, for example, changing the temperature of a solution containing only the first nucleic acid probe and the single-stranded nucleic acid molecule having a first type of base sequence from a high temperature to a low temperature, and measuring absorbance or fluorescence intensity of the solution. The temperature over a range from the temperature at which the denatured first nucleic acid probe and single-stranded nucleic acid molecule having a first type of base sequence begin to form a hybrid to the temperature at which nearly the entire amounts thereof are in the form of hybrids as determined from the resulting melting curve can be taken to be the temperature at which the first nucleic acid probe is able to specifically hybridize with the single-stranded nucleic acid molecule having a first type of base sequence. The salt concentration at which the first nucleic acid probe is able to specifically hybridize with the single-stranded nucleic acid molecule having a first type of base sequence can be determined by similarly determining a melting curve by changing the salt concentration of the solution from a low concentration to a high concentration instead of changing temperature.

Tm (melting temperature) can typically be substituted for the temperature at which the first nucleic acid probe and single-stranded nucleic acid molecule having a first type of base sequence specifically hybridize. For example, the value of Tm (temperature at which 50% of double-stranded DNA dissociates into single-stranded DNA) of a region that hybridizes with a single-stranded nucleic acid molecule having a first type of base sequence can be calculated from base sequence information of the first nucleic acid probe by using primer/probe design software and the like. In the present invention, the temperature of the sample solution may be lowered to a temperature of within about $\pm 3°$ C. of the value of Tm of a region in the first nucleic acid probe having a base sequence complementary to a single-stranded nucleic acid molecule having a first type of base sequence.

In addition, in order to inhibit non-specific hybridization, the temperature of the sample solution may be lowered slowly when forming a hybrid. For example, after denaturing nucleic acid molecules by raising the temperature of the sample solution to 70° C. or higher, the liquid temperature of the sample solution can be lowered at a temperature lowering rate of 0.05° C./second or faster.

In the method for identifying polymorphism of nucleic acid molecules of the present invention, detection of the hybrid in (d) is performed in the presence of an oligonucleotide having a base sequence complementary to a base sequence of a type other than the first type in the polymorphic sequence (hereinafter, referred as "decoy nucleic acid of a type other than the first type"). Therefore, in the preparation of the sample solution in (a), the decoy nucleic acid with the type other than the first type is included in the sample solution, or the decoy nucleic acid of a type other than the first type is added to the sample solution before (c). In the method for identifying polymorphism of nucleic acid molecules of the present invention, it is preferable that the decoy nucleic acid of a type other than the first type is added to the sample solution when the sample solution is prepared in (a), since formation of non-specific hybrids can be suppressed by the first nucleic acid probe in (b).

The amount of the decoy nucleic acid of a type other than the first type added to the sample solution is not particularly limited. However, it is preferable that the amount is excess to the target polymorphic nucleic acids. For example, it is preferable that the amount of the decoy nucleic acid is about 5-fold or more relative to the amount of the target polymorphic nucleic acids. The non-specific hybridization between the added nucleic acid probe and the nucleic acid molecules having other types can be effectively suppressed since there is excess amount of oligonucleotides specifically hybridizing with the nucleic acid molecules of the other type in the sample solution.

Additionally, it is preferable that surfactants, formamide, dimethylsulfoxide, or urea is added to the sample solution in advance before (c) in order to suppress the non-specific hybridization. These compounds can be added solely, or added as a combination of two or more of the compounds. Formation of the non-specific hybridization can be suppressed by adding these compound in a condition where temperature is relatively low. These compounds can be included in the sample solution during preparation of the sample solution in (a), or added to the sample solution after (b) and before (c).

Subsequently, in step (c), the number of molecules of hybrid containing the first nucleic acid probe is calculated by the scanning molecule counting method. More specifically, following the formation of hybrid, the number of molecules of hybrid is calculated by placing the sample solution in a photometric analysis device for carrying out the aforementioned scanning molecule counting method and then detecting and analyzing fluorescence emitted from the hybrid using the previously described technique.

Finally, the polymorphism of the target nucleic acid molecule is identified based on the result of (c) as (d). If a polymorphic nucleic acid molecule of the first type is included in the sample solution, the hybrid including the first nucleic acid probe is detected in (c).

For example, in a case where a somatic cell mutation or single nucleotide polymorphism is identified, whether the target nucleic acid molecule is the wild type or a mutation type (presence or absence of the somatic cell mutation) is determined by configuring the mutation type to be the first type and using the mutation type probe (Mt probe) specifically hybridizing with the nucleic acid molecule of the mutation type.

In addition, the polymorphic nucleic acid molecule can be identified more accurately by configuring each type among the polymorphic sequence to be the first type and performing the method for identifying polymorphism of the nucleic acid molecules of the present invention to all of the each type. For example, in a case where single nucleotide polymorphism is identified, the polymorphic nucleic acid can be identified more accurately by performing the method for identifying polymorphism of nucleic acid molecules of the present invention configuring the mutation type to be the first type, performing the method for identifying polymorphism of nucleic acid molecules of the present invention configuring the wild type to be the first type, and comparing the results obtained by the two analyses. Specifically, (a) to (c) are performed using the mutation type probe (Mt probe) specifically hybridizing with the mutation type nucleic acid molecule and an oligonucleotide having a base sequence complementary to that of the wild type (decoy nucleotide of the wild type). In addition, (a) to (c) are performed using the wild type probe (Wt probe) specifically hybridizing with the wild type nucleic acid molecule and an oligonucleotide having a base sequence complementary to that of the mutation type (decoy nucleotide of the mutation type) independently to (a) to (c). Whether the target nucleic acid molecule is the mutation type or the wild type is determined based on the calculated results of the molecule numbers of the hybrids including Mt probe and Wt probe. In a case where the target nucleic acid molecule is the mutation type, the number of the hybrids including Mt probe exceeds the number of the hybrids including Wt probe significantly, since the hybrids are formed preferentially with Mt probe.

(a) to (c) using Mt probe and (a) to (c) using Wt probe can be performed independently. Also, they can be performed at substantially the same time. For example, formed hybrids can be counted by preparing the sample solution, to which Wt probe, the target nucleic acid molecule, and the decoy nucleic acid of the mutation type are added, and forming hybrids of the nucleic acids in the sample solution, after preparing sample solution, to which Mt probe, the target nucleic acid molecule, and the decoy nucleic acid of the wild type are added, forming hybrids of the nucleic acids in the sample solution, and counting the formed hybrids. Also, they can be analyzed sequentially by placing the sample solutions to an optical analyzer. In this case, the sample solution, to which Mt probe, the target nucleotide molecules, and the decoy nucleic acid of the wild type, and the sample solution, to which Wt probe, the target nucleic acid molecule, and the decoy nucleic acid of the mutation type, are prepared first. Then, forming hybrids are performed simultaneously in the both samples solutions by decreasing their temperature gradually after increasing their temperature at the same time. Alternatively, the numbers of the hybrids including Wt probe and Mt probe can be counted separately in a single sample solution after adding the target nucleic acid molecule, Wt probe, Mt probe, the decoy nucleic acid of the mutation type, and the decoy nucleic acid of the wild type in a single sample solution, and forming hybrids of the nucleic acids in the sample solution.

For example, in the case of identifying a single nucleotide polymorphism, the number of molecules of a hybrid containing a wild type probe formed in the case of having added a wild type probe, and the number of molecules of a hybrid containing a mutant type probe are calculated by using a control single-stranded nucleic acid molecule having a known polymorphic sequence instead of a target nucleic acid molecule. A wild type nucleic acid molecule, mutant type nucleic acid molecule or equimolar mixture of a wild type nucleic acid molecule and mutant type nucleic acid molecule are respectively used for the control single-stranded nucleic acid molecule, and a nucleic acid alone is further added as a negative control. Information required for clustering the relationship between polymorphism of the control single-stranded nucleic acid molecule and hybrids can be acquired from each of the measurement results.

Figure 8:
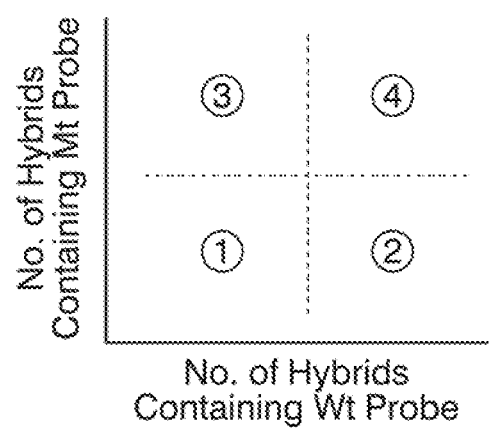
FIG. 8 is a drawing schematically showing an example of cluster rings based on the number of polymorphisms and hybrids.

FIG. 8 schematically shows an example of clustering based on polymorphism and the number of molecules of hybrids. In a sample solution to which only a nucleic acid probe has been added, the number of hybrids containing the Wt probe and the number of hybrids containing the Mt probe are both low (Cluster 1 in FIG. 8). In contrast, in a sample solution to which has been added a wild type nucleic acid molecule, the number of molecules of a hybrid containing the Wt probe is clearly greater than the number of molecules of a hybrid containing the Mt probe (Cluster 2 in FIG. 8). Conversely, in a sample solution to which has been added a mutant type nucleic acid molecule, the number of molecules of a hybrid containing the Mt probe is clearly greater than the number of molecules of a hybrid containing the Wt probe (Cluster 3 in FIG. 8). In a sample solution to which has been added an equimolar mixture of the wild type nucleic acid probe and the mutant type nucleic acid probe, both the number of molecules of a hybrid containing the Wt probe and the number of molecules of a hybrid containing the Mt probe increase (Cluster 4 in FIG. 8). Which polymorphism a target nucleic acid molecule is applicable to can be identified by comparing the results of clustering and the results in the case of having added the target nucleic acid molecule.

Alternatively, in the method for identifying polymorphism of nucleic acid molecules of the present invention, a single-stranded nucleic acid molecule including a base sequence of the first type and other nucleic acid probe designed so as to hybridize specifically with a region other than the polymorphic sequence region can be used with the first nucleic acid probe (the second nucleic acid probe). The second nucleic acid probe designed as explained above binds to the region other than the polymorphic sequence in the nucleic acid molecule with the polymorphic sequence. Thus, it form a hybrid with a nucleic acid molecule whose genotype is a type other than the first type among the polymorphic sequence. Therefore, by adding the second probe to the sample solution with the first nucleic acid probe and the target nucleic acid molecule and increasing the temperature of the sample solution, and then lowering the temperature gradually, hybrids including the first nucleic acid probe and hybrids including the second nucleic acid probe are formed in the sample solution in a case where the target nucleic acid molecule is the first type. On the other hand, in the case the target nucleic acid molecule is of the wild type, a hybrid that contains the first nucleic acid probe and the second nucleic acid probe is not formed although a hybrid containing the second nucleic acid probe is formed. Thus, in the case a hybrid containing the first nucleic acid probe and the second nucleic acid probe is formed in a sample solution, the target nucleic acid molecule can be identified to be of the first type, while in the case a hybrid is formed that does contain the second nucleic acid probe but does not contain the first nucleic acid probe, the target nucleic acid molecule can be identified to be of a type other than a first type in a polymorphic sequence.

In the case a target nucleic acid molecule forms a double-stranded nucleic acid molecule in the manner of genomic DNA, the second nucleic acid probe can be designed so as to specifically hybridize with a single-stranded nucleic acid molecule containing the first type of base sequence as previously described, or can be designed so as to specifically hybridize with a single-stranded nucleic acid molecule having a base sequence complementary to the single-stranded nucleic acid molecule containing the first type of base sequence (namely, a single-stranded nucleic acid molecule that hybrids with a single-stranded nucleic acid molecule having a polymorphic sequence). In the latter case as well, the second nucleic acid probe hybridizes with the single-stranded nucleic acid which is the complementary stranded of the single-stranded nucleic acid molecule having a polymorphic sequence in a region in which the base sequence is shared between polymorphic sequences. In other words, the second nucleic acid probe hybridizes with the single-stranded nucleic acid molecule having a polymorphic sequence regardless of the type of polymorphic sequence, forming the hybrid with the single-stranded nucleic acid molecule constituting the double-stranded nucleic acid molecule. Consequently, by adding both the first nucleic acid probe and the second nucleic acid probe to a sample solution in which the single stranded nucleic acid molecule containing the first type of base sequence is present as a double-stranded nucleic acid molecule (hybrid) made of the single-stranded nucleic acid molecule and a complementary single-stranded nucleic acid molecule, and by increasing the temperature in the sample solution at the same time and then lowering it gradually, the single-stranded nucleic acid molecule containing the first type of base sequence hybridizes with the first nucleic acid probe, while the complementary strand of the single-stranded nucleic acid molecule hybridizes with the second nucleic acid probe. On the other hand, in the case the target nucleic acid molecule is of a type other than the first type in a polymorphic sequence, only a hybrid containing the second nucleic acid probe is formed as a result of similar treatment, while a hybrid containing the first nucleic acid probe is not formed. Thus, in the case both a hybrid containing the first nucleic acid probe and a hybrid containing the second nucleic acid probe are formed in a sample solution, the target nucleic acid molecule can be identified to be of the first type, while in the case a hybrid containing the second nucleic acid probe is formed but a hybrid containing the first nucleic acid probe is not formed, the target nucleic acid molecule can be identified to be of a type other than the first type in the polymorphic sequence.

By designing the second nucleic acid probe so as to form a hybrid with a single-stranded nucleic acid molecule having a polymorphic sequence or with a complementary strand of that single-stranded nucleic acid molecule regardless of the type of polymorphic sequence, the proportion of single-stranded nucleic acid molecule that contains a first type of base sequence in the polymorphic sequence present in a sample solution can be calculated. For example, in the case of taking an SNP having two types consisting of a wild type and a mutant type to be a polymorphic sequence, taking the mutant type to be the first type and carrying out the method for identifying polymorphism of nucleic acid molecules of the present invention on a sample solution containing genomic DNA of a subject, in the case the number of hybrids containing the first nucleic acid probe is roughly equal to the number of hybrids containing the second nucleic acid probe, the genotype of the subject can be identified as being homogeneous for the mutant type. In the case the number of hybrids containing the first nucleic acid probe is significantly less than the number of hybrids containing the second nucleic acid probe, the genotype of the subject can be identified as being heterogeneous, and in the case hybrids containing the first nucleic acid probe are hardly detected at all, the genotype of the subject can be identified as being homogeneous for the wild type.

In addition, by designing the second nucleic acid probe so as to form a hybrid with a single-stranded nucleic acid molecule having a polymorphic sequence or with a complementary strand of that single-stranded nucleic acid molecule, this method can also be used to evaluate the accuracy of a measurement system. For example, in the case a hybrid containing the second nucleic acid probe is hardly detected at all, it is possible that a polymorphic nucleic acid is not contained in the sample solution used in an amount sufficient for measurement or that the measurement system is not functioning properly, thereby suggesting that reliable results cannot be obtained.

The hybrids including the first nucleic acid probe and the hybrid including the second nucleic acid probe can be detected separately by emitted light after making the optical characteristics of the index fluorescence for detecting the hybrids including the second nucleic acid probe different from that for detecting the hybrids including the first nucleic acid probe.

Although the following provides a more detailed explanation of the present invention by indicating examples thereof, the present invention is not limited to the following examples.

Although the following provides a more detailed explanation of the present invention by indicating examples thereof, the present invention is not limited to the following examples.

EXAMPLE 1

The ability to identify a codon 12_GTT mutation of K-ras gene with the scanning molecule counting method was verified using one type of molecular beacon probe.

A nucleic acid molecule having the base sequence described in Table 1 (SEQ ID NO: 1), in which TAMRA was added to the 5'-terminal and BHQ-2 was added to the 3'-terminal, was used as a mutant type (GTT) molecular beacon probe. In addition, a wild type (GGT) nucleic acid (SEQ ID NO: 2) alone having a base sequence similarly described in Table 1 (mutation rate: 0%), a mixture of wild type (GGT) nucleic acid and mutant type (GTT) nucleic acid (SEQ ID NO: 3) mixed at a molar ratio of 9:1 (mutation rate: 10%), and a mutant type (GTT) nucleic acid alone (mutation rate: 100%) were used as target nucleic acid molecules. Moreover, a non-fluorescence-labeled probe (wild type (GGT) decoy nucleic acid) (SEQ ID NO: 4) having a base sequence complementary to the wild type (GGT) nucleic acid was used to inhibit non-specific hybridization. The synthesis of these oligo-nucleotides was commissioned to Sigma Genosys Inc. In Table 1, the sequence number is shown in the right-hand column of the table. In addition, those bases shown in boldface type in Table 1 indicate mutation sites or bases that form base pairs with mutation sites. Moreover, the underlined bases in the mutant type (GTT) molecular beacon probe indicate those regions that mutually hybridize when forming an intramolecular structure.

TABLE 1

| | Base Sequence | |
|---|---|---|
| Mutant type (GTT) molecular beacon probe | TAMRA-<u>CCTACGCC</u> AAC AGCTCCAACTA<u>CGTAGG</u>-BHQ2 | 1 |
| Wild type (GGT) nucleic acid | TGACTGAATATAAACTTGTGGTAGTTGGAGCT GGT GGCGTAGGCA | 2 |
| Mutant type (GTT) nucleic acid | TGACTGAATATAAACTTGTGGTAGTTGGAGCT GTT GGCGTAGGCA | 3 |
| Wild type (GGT) decoy nucleic acid | CCTACGGCC ACC AGCTCCAACTAC | 4 |

The aforementioned mutant type (GTT) molecular beacon probe, target nucleic acid molecules and wild type decoy nucleic acid were dissolved in Tris buffer (10 mM Tris-HCl, 1 mM EDTA and 400 mM NaCl, pH 8.0) to concentrations of 100 µM, 100 nM (total concentration of wild type and mutant type) and 500 nM, respectively, to prepare sample solutions.

After denaturing the prepared sample solutions by heating for 5 minutes at 95° C., hybrids were formed by gradually lowering the liquid temperature to 20° C. More specifically, temperature lowering treatment was carried out for 5 minutes at 90° C., 10 minutes at 80° C., 10 minutes at 70° C., 10 minutes at 60° C., 10 minutes at 50° C., 10 minutes at 40° C. and 10 minutes at 30° C. at a temperature lowering rate of 0.1° C./second.

The numbers of molecules of hybrids in the sample solutions following temperature lowering treatment were counted by the scanning molecule counting method. More specifically, during measurement, chronological photon counting data was acquired for each of the aforementioned sample solutions using the MF20 Single Molecule Fluorescence Spectroscopy System (Olympus Corp.) provided with confocal fluorescence microscope optics and a photon counting system as a photometric analysis device. At that time, the sample solutions were irradiated with excitation light at 300 µW using laser light having a wavelength of 543 nm, while the sample solutions were irradiated with detection light having a wavelength of 560 nm to 620 nm using a band pass filter. The movement speed of the location of the photodetection region in the sample solutions was set to 15 mm/second, bin time was set to 10 µsec, and measurement time was set to 2 seconds. In addition, measurements were carried out 5 times on each sample followed by calculation of the mean and standard deviation thereof. Following measurement of luminous intensity, optical signals detected in chronological data were counted from the chronological photon count data acquired for each sample solution. During smoothing of the data using the moving average method, a total of 9 data points were averaged at one time, and moving average processing was repeated 5 times. In addition, during fitting, a Gaussian function was fit to the chronological data using the least squares method followed by determination of peak intensity, peak width (full width half maximum) and correlation coefficient (in the Gaussian function). Moreover, during peak evaluation processing, only those peaks that satisfied the following conditions:

20 µsec<peak width<400 µsec
peak intensity>1(photon/10 µsec) and
correlation coefficient>0.95 were judged to be optical signals corresponding to the target nucleic acid molecules, while peak signals that did not satisfy the aforementioned conditions were treated as noise and ignored, and the number of signals judged to be optical signals corresponding to the target nucleic acid molecules were counted as the number of peaks.

Figure 9:
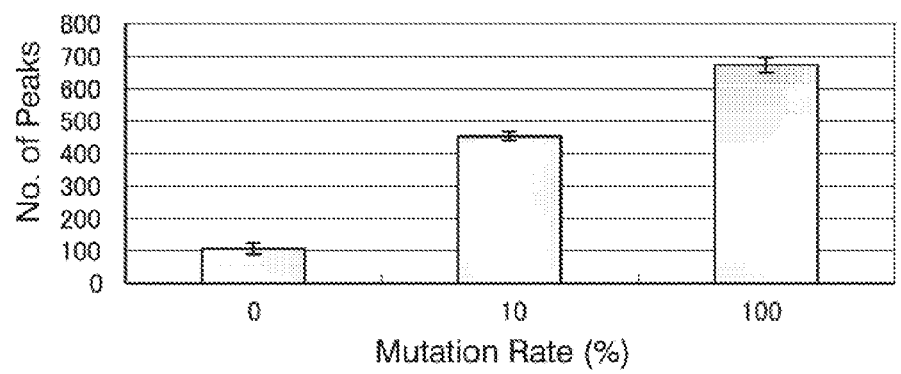
FIG. 9 is a drawing indicating the values of the number of peaks counted for each GTT mutation rate in target nucleic acid molecules added to sample solutions in Example 1.

FIG. 9 indicates values for the number of peaks counted for each GTT mutation rate in the target nucleic acid molecules added to the sample solutions. As a result, since the number of peaks increases dependent on GTT mutation rate, the mutant type (GTT) molecular beacon probe was confirmed to specifically hybridize with the GTT mutation sequence.

EXAMPLE 2

The detection frequency of hybrids containing a nucleic acid probe was investigated by adding nucleic acid molecules having a base sequence complementary to a polymorphic sequence of a type other than a type specifically bound by the nucleic acid probe to sample solutions.

More specifically, the mutant type (GTT) molecular beacon probe, target nucleic acid molecules and wild type (GGT) decoy nucleic acid used in Example 1 were dissolved in Tris buffer (10 mM Tris-HCl, 1 mM EDTA and 100 mM NaCl, pH 8.0) to concentrations of 100 pM, 100 nM (total concentration of wild type and mutant type) and 1 µM, respectively, to prepare sample solutions. On the other hand, a sample solution not containing wild type (GGT) decoy nucleic acid was prepared in the same manner with the exception of not adding the wild type (GGT) decoy nucleic acid.

Hybrids were formed after denaturing the nucleic acid molecules in the sample solutions by raising and lowering the liquid temperature of these sample solutions in the same manner as Example 1, and the numbers of molecules of hybrids containing the mutant type (GTT) molecular beacon probe in the sample solutions were counted under the same conditions as Example 1.

Figure 10:
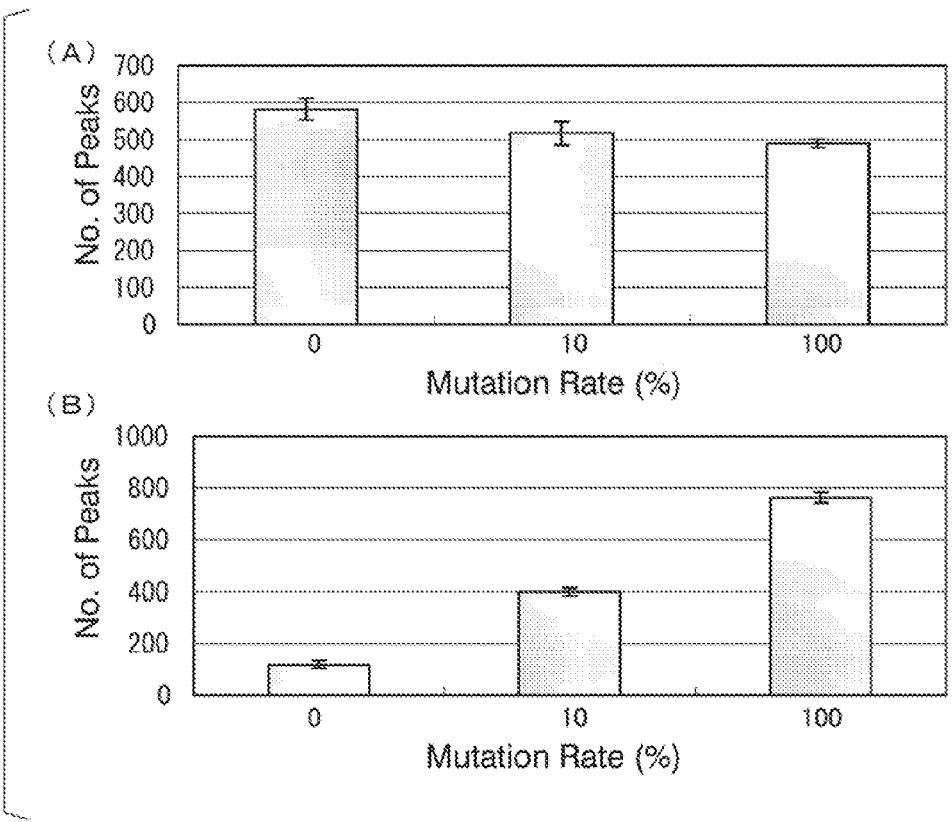
FIGS. 10(A) and 10(B) are a drawing indicating the values of the number of peaks counted for each GTT mutation rate in target nucleic acid molecules added to a sample solution to which a decoy nucleic acid was not added in Example 2, and a drawing indicating the values of the number of peaks counted for each GTT mutation rate in target nucleic acid molecules added to a sample solution to which was added a decoy nucleic acid in Example 2, respectively.

FIG. 10 indicates values for the number of peaks counted for each GTT mutation rate in the target nucleic acid molecules added to the sample solutions. FIG. 10(A) indicates results for the sample solution to which wild type (GGT) decoy nucleic acid was not added, while FIG. 10(B) indicates results for the sample solution to which wild type (GGT) decoy nucleic acid was added. As a result, the number of peaks had already increased when the mutation rate was 0% in the absence of the wild type (GGT) decoy nucleic acid as shown in FIG. 10(A). This suggests that the mutant type (GTT) molecular beacon probe non-specifically hybridized with the wild type (GGT) nucleic acid as well. On the other hand, as shown in FIG. 10(B), since the number of peaks increased dependent on the mutation rate in the presence of the wild type (GGT) decoy nucleic acid, this suggests that the mutant type (GTT) molecular beacon probe specifically hybridized with the mutant type (GTT) nucleic acid. On the basis of these results, non-specific hybridization of a molecular beacon probe was clearly demonstrated to be able to be inhibited by adding a decoy nucleic acid to the sample solution.

EXAMPLE 3

Respective genotypes were identified by using the mutant type (GTT) molecular beacon probe used in Example 1 and a wild type (GGT) molecular beacon probe.

A nucleic acid molecule having a base sequence described in Table 2 (SEQ ID NO: 5) in which TAMRA was added to the 5'-terminal and BHQ-2 was added to the 3'-terminal was used for the wild type (GGT) molecular beacon probe.

In addition to the wild type (GGT) nucleic acid alone (mutation rate: 0%) and the mutant type (GTT) nucleic acid alone (mutation rate: 100%) used in Example 1, a mixture of wild type (GGT) nucleic acid and mutant type (GTT) nucleic acid mixed at a molar ratio of 1:1 (mutation rate: 50%) were used as target nucleic acid molecules. Moreover, the wild type (GGT) decoy nucleic acid used in Example 1 and a non-fluorescence-labeled probe having a base sequence complementary to the mutant type (GTT) nucleic acid (mutant type (GTT) decoy nucleic acid) (SEQ ID NO: 6) were used to inhibit non-specific hybridization. Table 2 shows the sequence of the mutant type (GTT) decoy nucleic acid. In Table 2, the sequence number is shown in the right-hand column of the table. In addition, those bases shown in boldface type in the table indicate mutation sites or bases that form base pairs with mutation sites, and the underlined bases indicate those regions that mutually hybridize when forming an intramolecular structure. Furthermore, synthesis of the oligonucleotides used in the present example was commissioned to Sigma Genosys Inc.

TABLE 2

| | Base Sequence | |
|---|---|---|
| Wild type (GGT) molecular beacon probe | TAMRA-<u>CCTACGCC</u> ACC AGCTCCAACTA<u>CGTAGG</u>-BHQ2 | 5 |
| Mutant type (GTT) decoy nucleic acid | CCTACGCC AAC AGCTCCAACTAC | 6 |

More specifically, the mutant type (GTT) molecular beacon probe, target nucleic acid molecules and wild type (GGT) decoy nucleic acid were dissolved in Tris buffer (10 mM Tris-HCl, 1 mM EDTA and 400 mM NaCl, pH 8.0) to concentrations of 100 pM, 100 nM (total concentration of wild type and mutant type) and 500 nM, respectively, to prepare sample solutions. In addition, a control sample solution was prepared in the same manner with the exception of not adding the target nucleic acid molecules.

On the other hand, the wild type (GGT) molecular beacon probe, target nucleic acid molecules and mutant type (GTT) decoy nucleic acid were dissolved in the aforementioned Tris buffer to concentrations of 100 pM, 100 nM (total concentration of wild type and mutant type) and 500 nM, respectively, to prepare sample solutions containing the wild type (GGT) molecular beacon probe and mutant type (GTT) decoy nucleic acid. In addition, a control sample solution was prepared in the same manner with the exception of not adding the target nucleic acid molecules.

Hybrids were formed after denaturing the nucleic acid molecules in the sample solutions by raising and lowering the liquid temperature of the respective sample solutions in the same manner as Example 1, and the numbers of molecules of hybrids containing the mutant type (GTT) molecular beacon probe and number of molecules of hybrids containing the wild type (GGT) molecular beacon probe in the sample solutions were respectively counted under the same conditions as Example 1.

Figure 11:
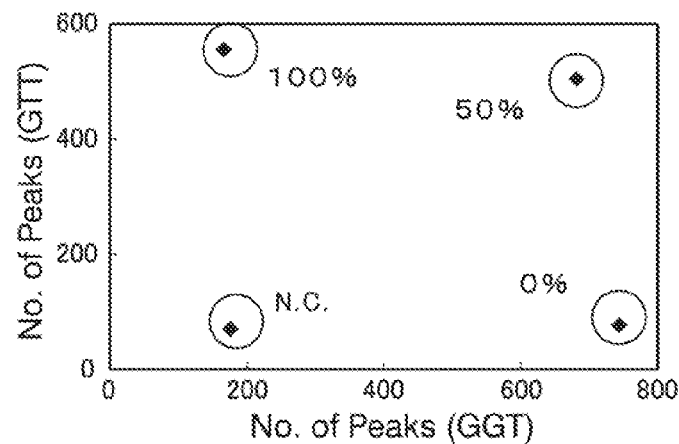
FIG. 11 is a drawing indicating the values of the number of peaks counted for each mutation rate in target nucleic acid molecules added to sample solutions in Example 3 by plotting the number of molecules of hybrids containing a mutant (GTT) molecular beacon probe (number of mutant (GTT) peaks) on the vertical axis, and plotting the number of molecules of hybrids containing a wild type (GGT) molecular beacon probe (number of wild type (GGT) peaks) on the horizontal axis.

FIG. 11 indicates values for the number of peaks counted for each mutation rate in the target nucleic acid molecules added to the sample solutions by plotting the number of molecules of hybrids containing the mutant type (GTT) molecular beacon probe (number of mutant type (GTT) peaks) (indicated by "Number of peaks (GTT)" in the drawing) on the vertical axis, and plotting the number of hybrids containing the wild type (GGT) molecular beacon probe (number of wild type (GGT) peaks) (indicated by "Number of peaks (GGT)" in the drawing) on the horizontal axis. As a result, the number of mutant type (GTT) peaks and the number of wild type (GGT) peaks were both extremely low in the control sample solution in which target nucleic acid molecules were not present (indicated by "N.C." in the drawing). On the other hand, although the number of mutant type (GTT) peaks was only roughly the same as that of the control sample solution in the sample solution having a GTT mutation rate of 0% (indicated by "0%" in the drawing), the number of wild type (GGT) peaks was extremely high. Conversely, although the number of wild type (GGT) peaks was only roughly the same as that of the control sample solution in the sample solution having a GTT mutation rate of 100% (indicated by "100%" in the drawing), the number of mutant type (GTT) peaks was extremely high. In contrast, both the numbers of wild type (GGT) peaks and mutant type (GTT) peaks were high in the sample solution having a GTT mutation rate of 50% (indicated by "50%" in the drawing). In this manner, three types of sample solutions having different GTT mutation rates were able to be mutually distinguished based on the number of wild type (GGT) peaks and the number of mutant type (GTT) peaks. On the basis of these results, identification of genetic mutations using the method for identifying polymorphism of nucleic acid molecules of the present invention was determined to enable identification of target nucleic acid molecules for each mutation rate, and make it possible to easily type the genotype of analyzed genomic DNA as to being homogeneous for the wild type, heterogeneous, or homogeneous for the mutant type particularly in analyses of single nucleotide polymorphisms.

EXAMPLE 4

A codon 12_GTT mutation of K-ras gene was identified in a condition where both hybrids including the mutant type (GTT) molecular beacon probe and the wild type (GGT) molecular beacon probe were formed in a single sample solution in the method for identifying polymorphism of nucleic acid molecules of the present invention.

An oligonucleotide composed of the same base sequence (SEQ ID NO: 1) as the mutant type (GTT) molecular beacon probe described in Table 1 having ATTO® 647N added to the 5'-terminal and BHQ-3 added to the 3'-terminal was used as a mutant type (GTT) molecular beacon probe. The wild type (GGT) molecular beacon probe, the target nucleic acid molecules used, the decoy nucleic acid of the wild type (GGT), and the decoy nucleotide of the mutation type (GTT) were the same as those used in Example 3. Synthesis of the oligonucleotides used in the present example was commissioned to Sigma Genosys Inc. Specifically, the mutant type (GTT) molecular beacon probe, the wild type (GGT) molecular beacon probe, the target nucleic acid molecule, the decoy nucleic acid of the wild type (GGT), and the decoy nucleotide of the mutation type (GTT) were dissolved in a Tris buffer (10 mM Tris-HCl, 1 mM EDTA, 400 mM NaCl, pH8.0) so as for their concentrations to be 100 pM, 100 pM, 100 nM (concentration of the sum of wild type and mutation type), 500 nM, and 500 nM, respectively. Also, the control sample solutions were prepared in the same manner except for not adding the target nucleic acid molecule.

Hybrids were respectively formed after denaturing the nucleic acid molecules in the sample solution by raising and lowering the liquid temperature of the sample solution in the same manner as Example 1. The numbers of hybrids in the sample solution after temperature lowering treatment were counted by the scanning molecule counting method. More specifically, in order to excite the TAMRA-labeled wild type (GGT) molecular beacon probe, the sample solution was irradiated with excitation light at 300 μW using laser light having a wavelength of 543 nm, and irradiated with detection light having a wavelength of 565 nm to 595 nm using a band pass filter. In order to excite the ATTO647N-labeled mutant type (GTT) molecular beacon probe, the sample solution was irradiated with excitation light at 300 μW using laser light having a wavelength of 633 nm, and irradiated with detection light having a wavelength of 650 nm to 690 nm using a band pass filter. For the remainder of the procedure, measurement and analyses were carried out by the scanning molecular counting method under the same conditions as Example 3.

Figure 12:
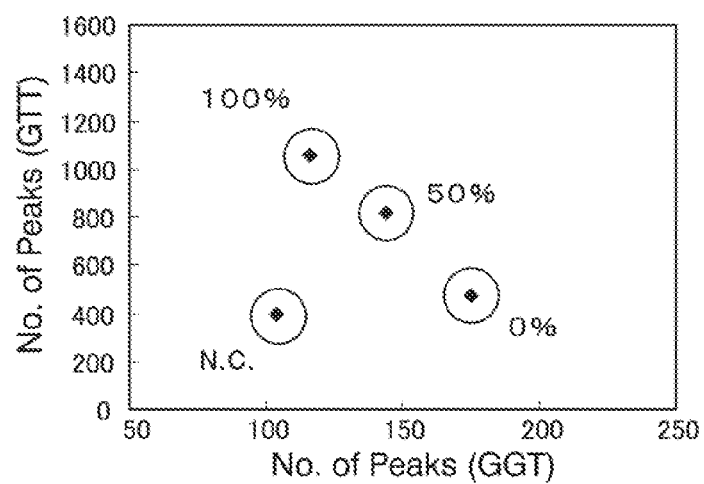
FIG. 12 is a drawing indicating the values of the number of peaks counted for each mutation rate in target nucleic acid molecules added to sample solutions in Example 3 by plotting the number of molecules of hybrids containing a mutant (GTT) molecular beacon probe (number of mutant (GTT) peaks) on the vertical axis, and plotting the number of molecules of hybrids containing a wild type (GGT) molecular beacon probe (number of wild type (GGT) peaks) on the horizontal axis.

FIG. 12 indicates values for the number of peaks counted for each mutation rate in the target nucleic acid molecules added to the sample solution by plotting the number of molecules of hybrids containing the mutant type (GTT) molecular beacon probe (number of mutant type (GTT) peaks) (indicated by "Number of peaks (GTT)" in the drawing) on the vertical axis, and plotting the number of hybrids containing the wild type (GGT) molecular beacon probe (number of wild type (GGT) peaks) (indicated by "Number of peaks (GGT)" in the drawing) on the horizontal axis. As a result, the number of mutant type (GTT) peaks and the number of wild type (GGT) peaks were both extremely low in the control sample solution in which target nucleic acid molecules were not present. On the other hand, although the number of mutant type (GTT) peaks was low, the number of wild type (GGT) peaks was extremely high. Conversely, although the number of wild type (GGT) peaks was low, the number of mutant type (GTT) peaks was high. In contrast, both the numbers of wild type (GGT) peaks and mutant type (GTT) peaks were high in the sample solution having a GTT mutation rate of 50%. In this manner, three types of sample solutions having different GTT mutation rates were able to be mutually distinguished based on the number of wild type (GGT) peaks and the number of mutant type (GTT) peaks. On the basis of these results, it is clear that the target nucleic acid molecules were identified for each mutation rate even in the case that both hybrids were formed and detected in a single sample solution as Example 7, in which hybridization and detection of the target nucleic acid molecule and the beacon probe of the mutation type (GTT) and those of the target nucleic acid molecule and the beacon probe of the wild type (GGT) were performed in different sample solutions.

EXAMPLE 5

The target nucleic acid molecules were identified for each mutation rate in Example 4. However, the distances of each spot of each sample solution in FIG. 12 is less than those of Example 3 shown in FIG. 11. This indicates that identification capability of the method performed in Example 4 is a bit less effective than the method performed in Example 3.

Therefore, the identification capability of the mutation rate was improved by adjusting the length of the decoy nucleic acids.

Specifically, the sample solutions were prepared as in Example 4 except for using the wild type (GGT) decoy nucleic acid (SEQ ID NO: 7) and the mutant type (GTT) decoy nucleic acid (SEQ ID NO: 8) shown in Table 3 instead of the wild type (GGT) decoy nucleic acid and the mutant type (GTT) decoy nucleic acid used in Example 4. The decoy nucleic acids used in the present Example is one base shorter than those used in Example 4. The numbers in the right column indicate their sequence identification numbers. Bases shown in the bold-type indicate that they are the mutated site or bases forming base parings with the mutated site.

TABLE 3

| | Base Sequence | |
|---|---|---|
| Wild type (GGT) decoy nucleic acid | CCTACGCC ACC AGCTCCAACTA | 7 |
| Mutant type (GTT) decoy nucleic acid | CCTACGCC AAC AGCTCCAACTA | 8 |

Hybrids were respectively formed after denaturing the nucleic acid molecules in the sample solutions by raising and lowering the liquid temperature of the sample solutions in the same manner as Example 4, and the number of molecules of hybrids containing the mutant type (GTT) molecular beacon probe and the number of molecules of hybrids containing the wild type (GGT) molecular beacon probe in the sample solutions were respectively counted under the same conditions as Example 4.

Figure 13:
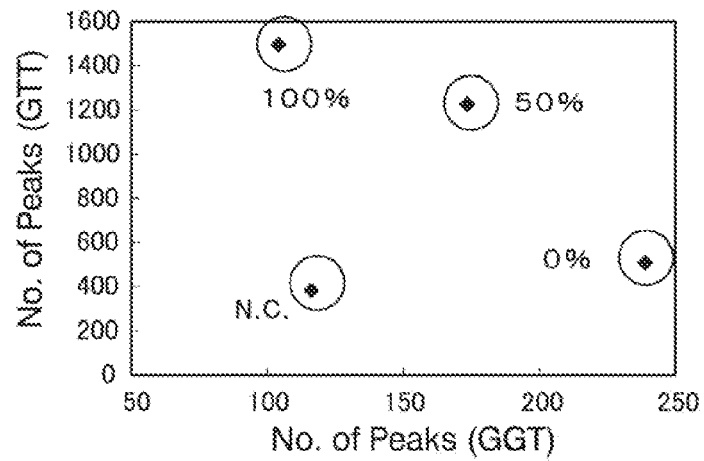
FIG. 13 is a drawing indicating the values of the number of peaks counted for each mutation rate in target nucleic acid molecules added to sample solutions in Example 5 by plotting the number of molecules of hybrids containing a mutant (GTT) molecular beacon probe (number of mutant (GTT) peaks) on the vertical axis, and plotting the number of molecules of hybrids containing a wild type (GGT) molecular beacon probe (number of wild type (GGT) peaks) on the horizontal axis.

FIG. 13 indicates values for the number of peaks counted for each mutation rate in the target nucleic acid molecules added to the sample solutions by plotting the number of molecules of hybrids containing the mutant type (GTT) molecular beacon probe (number of mutant type (GTT) peaks) (indicated by "Number of peaks (GTT)" in the drawing) on the vertical axis, and plotting the number of hybrids containing the wild type (GGT) molecular beacon probe (number of wild type (GGT) peaks) (indicated by "Number of peaks (GGT)" in the drawing) on the horizontal axis. As a result, the distances between spots of each sample solution were increased compared to Example 4 indicated by FIG. 12 and the identification capability of the GTT mutation rate in the sample solution was determined.

It is believed that the reason for the lower identification capability in Example 4 than Example 3 is due to inhibiting of not only the non-specific binding of the decoy nucleic acid with the target sequence but the specific binding, since two kinds of molecular beacon probes and two kinds of decoy nucleic acids were co-existed. In the present Example, it is interpreted that the identification capability of the GTT mutation rate was improved since the inhibition of specific binding of the molecular beacon with the target sequence was reduced due to shortening the length of the decoy nucleic acids.

Based on this result, it is clear that polymorphism can be identified very accurately even in the case where formation and detection of hybrids including both of the mutant type (GTT) molecular beacon probe and the wild type (GGT) molecular beacon probe were performed when the nucleic acid probe specific to the first type of the polymorphic sequence and the nucleic acid probe specific to the other type of the polymorphic sequence were co-existed in a single sample solution by optimizing decoy nucleic acid design.

EXAMPLE 6

A codon 12_GTT mutation of K-ras gene was identified using a nucleic acid probe, which has a base sequence differing from that of the first nucleic acid probe and does not recognize a polymorphic site composed of a target polymorphic sequence, as the second nucleic acid probe with the first nucleic acid probe.

More specifically, a common molecular beacon probe was used for the second nucleic acid probe that is a region of K-ras gene that does not contain codon 12, and was obtained by adding ATTO® 647N to the 5'-terminal and adding BHQ-3 to the 3'-terminal of an oligonucleotide (SEQ ID NO: 10) that specifically hybridizes with a base sequence (SEQ ID NO: 9; common sequence) of a region common to the wild type and mutant type. In addition, an oligonucleotide composed of the aforementioned common sequence was used as a common nucleic acid. In Table 4, nucleotide sequence of the common molecular beacon probe and the common sequence are shown. In Table 4, the sequence number is shown in the right-hand column of the table. In addition, the underlined bases in the common molecular beacon probe indicate those regions that mutually hybridize when forming an intramolecular structure.

TABLE 4

|  | Base Sequence |  |
|---|---|---|
| Common sequence | TCTGAATTAGCTGTATCGTCAAGGCACTCTTGCCTAC | 9 |
| Common molecular beacon probe | ATTO647N-<u>GCCTTGA</u>CGATACAGCTAAT<u>TCAAGGC</u>-BHQ3 | 10 |

In addition, the mutant type (GTT) molecular beacon probe used in Example 1 was used for the first nucleic acid probe. In addition, the wild type (GGT) nucleic acid alone (mutation rate: 0%) and the mutant type (GTT) nucleic acid alone (mutation rate: 100%) used in Example 1 were used for the target nucleic acid molecules. Moreover, the wild type (GGT) decoy nucleic acid used in Example 1 was used to inhibit non-specific hybridization. Furthermore, synthesis of the oligonucleotides used in the present example was commissioned to Sigma Genosys Inc.

More specifically, the mutant type (GTT) molecular beacon probe, common molecular beacon probe, wild type (GGT) nucleic acid or mutant type (GTT) nucleic acid, common nucleic acid and wild type (GGT) decoy nucleic acid were dissolved in Iris buffer (10 mM Tris-HCl, 1 mM EDTA, 400 mM NaCl, pH 8.0) to concentrations of 100 pM, 100 pM, 100 nM, 100 nM and 500 nM, respectively, to prepare sample solutions. In addition, a control sample solution was prepared in the same manner with the exception of not adding both the wild type (GGT) nucleic acid and mutant type (GTT) nucleic acid.

Hybrids were respectively formed after denaturing the nucleic acid molecules in the sample solutions by raising and lowering the liquid temperature of the sample solutions in the same manner as Example 1, and the number of molecules of hybrids containing the mutant type (GTT) molecular beacon probe and the number of molecules of hybrids containing the wild type (GGT) molecular beacon probe in the sample solutions were respectively counted under the same conditions as Example 5.

FIG. 14 indicates values for the number of peaks counted for each GTT mutation rate in the target nucleic acid molecules added to the sample solutions. FIG. 14(A) indicates the results of counting hybrids containing the mutant type (GTT) molecular beacon probe, while FIG. 14(B) indicates the results of counting hybrids containing the common molecular beacon probe. In the case of detecting fluorescence of TAMRA by exciting at 543 nm, a significant difference appeared in the counted number of hybrids containing the mutant type (GTT) molecular beacon probe between a mutation rate of 0% (addition of wild type (GGT) nucleic acid alone) and a mutation rate of 100% (addition of mutant type (GTT) nucleic acid alone), and both were able to be identified. In addition, in the case of detecting fluorescence of ATTO647N by exciting at 633 nm, a significant difference appeared between a mutation rate of 0% and a mutation rate of 100% in comparison with the results for the control sample solution to which target nucleic acid molecules were not added (indicated by "N.C." in the drawing).

In the present example, although a common nucleic acid was added to a sample solution separate from a wild type (GGT) nucleic acid and mutant type (GTT) nucleic acid, in the case the target nucleic acid molecule is genomic DNA or in the case it is DNA amplified from genomic DNA by PCR and the like, the common sequence and polymorphic sequence are present on the same single-stranded nucleic acid molecule or complementary strand of that single-stranded nucleic acid molecule. Consequently, in the case of using a probe that hybridizes with a region common to polymorphic sequences for the second nucleic acid probe as in the present example, whether or not a nucleic acid molecule containing a target polymorphic sequence is present in the sample solution can be confirmed based on the presence or absence of a hybrid containing the second nucleic acid probe. In addition, the amount of nucleic acid molecules attributable to variations in the amount amplified by PCR can be corrected according to the detected amount of a hybrid containing the second nucleic acid probe, thereby making it possible to improve the accuracy of polymorphism identification.

EXAMPLE 7

The ability to identify a codon 12_GTT mutation of K-ras gene with the scanning molecule counting method was verified using one type of nucleic acid probe and a fluorescent intercalator.

A nucleic acid molecule having the base sequence described in Table 5 (SEQ ID NO: 11), in which ROX was added to the 5'-terminal, was used as a mutant type (GTT) probe. In Table 5, the sequence number is shown in the right-hand column of the table, and those bases shown in boldface type indicate mutation sites or bases that form base pairs with mutation sites. Moreover, the wild type (GGT) nucleic acid and mutant type (GTT) nucleic acid used in Example 1 were used as target nucleic acid molecule.

TABLE 5

| | Base Sequence | |
|---|---|---|
| Mutant type (GTT) probe | ROX-CCTACGCC AAC AGCTCCAACTAC | 11 |

More specifically, the mutant type (GTT) probe, wild type (GGT) nucleic acid or mutant type (GTT) nucleic acid, and a wild type (GGT) decoy nucleic acid were dissolved in Tris buffer (10 mM Tris-HCl, 1 mM EDTA and 100 mM NaCl, pH 8.0) to concentrations of 100 pM, 100 pM and 1 nM, respectively, to prepare sample solutions. On the other hand, a sample solution not containing the wild type (GGT) decoy nucleic acid was prepared in the same manner with the exception of not adding the wild type (GGT) decoy nucleic acid.

Hybrids were formed by denaturing the prepared sample solutions by heating for 5 minutes at 94° C., followed by lowering the temperature at the rate of 0.1° C./second and treating at a constant temperature of 68.8° C. for 5 minutes.

A solution obtained by diluting PicoGreen (Molecular Probes, Inc.) by a factor of 1000 with the aforementioned Tris buffer was respectively added to these concentrated sample solutions to prepare 10-fold dilutions of the concentrated sample solutions, which were then used as sample solutions. The sample solutions were allowed to stand for 30 minutes or more after adding the diluted PicoGreen solution.

Subsequently, the numbers of molecules of hybrids in the sample solutions were counted by the scanning molecule counting method. More specifically, during measurement, chronological photon counting data was acquired for each of the aforementioned sample solutions using the MF20 Single Molecule Fluorescence Spectroscopy System (Olympus Corp.) provided with confocal fluorescence microscope optics and a photon counting system as a photometric analysis device. At that time, the sample solutions were irradiated with excitation light at 100 µW and a rotating speed of 6,000 rpm using laser light having a wavelength of 488 nm, and irradiated with detection light having a wavelength of 560 nm to 620 nm using a band pass filter. Signals obtained from an avalanche diode were set to a bin time of 10 µsec, and measurement time was set to 2 seconds.

After smoothing the chronological data obtained from the measurements with the Savinzky-Golay algorithm, peaks were detected by differentiation. Those regions considered to be peaks that were able to be approximated to a Gaussian function were extracted as signals. A comparison was then made between the number of peaks obtained in samples to which the wild type (GGT) decoy nucleic acid was added and samples to which it was not added.

Figure 15:
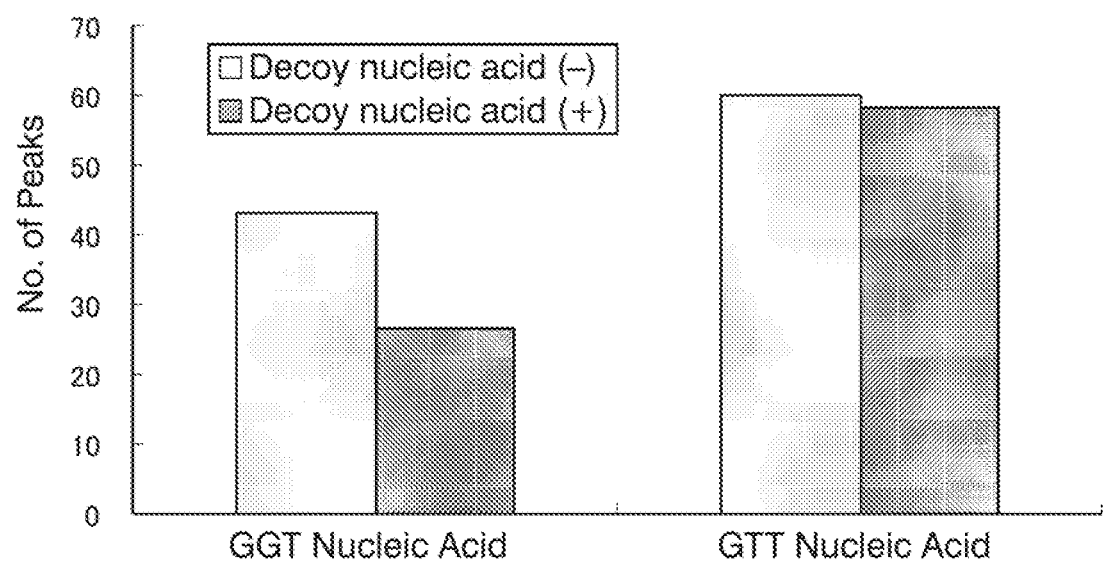
FIG. 15 is a drawing indicating the values of the number of peaks counted for each mutation rate in target nucleic acid molecules added to sample solutions in Example 7.

FIG. 15 indicates values for the number of peaks counted for each target nucleic acid molecule added to the sample solutions. As a result, although there was little difference in the number of peaks according to whether or not the wild type (GGT) decoy nucleic acid was added in the sample solution to which mutant type (GTT) nucleic acid was added (indicated by "GTT Nucleic Acid" in the drawing), in the sample solution to which wild type (GGT) nucleic acid was added (indicated by "GGT Nucleic Acid" in the drawing), the number of peaks was clearly higher in the sample solution to which wild type (GGT) decoy nucleic acid was not added in comparison with the sample solution to which wild type (GGT) decoy nucleic acid was added. This result is thought to be due to the promotion of sequence-specific binding as a result of non-specific binding of the mutant type (GTT) probe with the wild type (GGT) nucleic acid having been inhibited by the wild type (GGT) decoy nucleic acid having specifically bound with the wild type (GGT) nucleic acid. Namely, on the basis of these results, identification accuracy of the nucleic acid probe was clearly improved by adding to the sample solution a nucleic acid molecule having a base sequence complementary to a base sequence of a type other than a type specifically bound by the nucleic acid probe in a polymorphic sequence.

Example 8

A codon 12_GTT mutation of K-ras gene was identified with the scanning molecule counting method using the mutant type (GTT) probe used in Example 7, a wild type (GGT) probe and a fluorescent intercalator.

A nucleic acid molecule having the base sequence described in Table 6 (SEQ ID NO: 12), in which ROX was added to the 5'-terminal, was used as a wild type (GGT) probe. In Table 6, the sequence number is shown in the right-hand column of the table, and those bases shown in boldface type indicate mutation (polymorphic) sites or bases that form base pairs with mutation sites. In addition, a wild type (GGT) nucleic acid (SEQ ID NO: 2) alone (mutation rate: 0%) having the base sequence described in Table 1, a mixture of wild type (GGT) nucleic acid and mutant type (GTT) nucleic acid (SEQ ID NO: 3) mixed at a molar ratio of 9:1 (mutation rate: 10%), a mixture of wild type (GGT) nucleic acid and mutant type (GTT) nucleic acid (SEQ ID NO: 3) mixed at a molar ratio of 1:1 (mutation rate: 50%), and a mutant type (GTT) nucleic acid alone (mutation rate: 100%) were used as target nucleic acid molecules. Moreover, the mutant type (GTT) decoy nucleic acid used in Example 3 was used to inhibit non-specific hybridization.

TABLE 6

| | Base Sequence | |
|---|---|---|
| Wild type (GGT) probe | ROX-CCTACGCC ACC AGCTCCAACTAC | 12 |

More specifically, the mutant type (GTT) probe, target nucleic acid molecules, and wild type (GGT) decoy nucleic acid were dissolved in Tris buffer (10 mM Tris-HCl, 1 mM EDTA and 100 mM NaCl, pH 8.0) to concentrations of 100 pM, 100 pM and 1 nM, respectively, to prepare sample solutions containing the mutant type (GTT) probe and the wild type (GGT) decoy nucleic acid. On the other hand, the wild type (GGT) probe, target nucleic acid molecules and mutant type (GTT) decoy nucleic acid were dissolved in the aforementioned Tris buffer to concentrations of 100 pM, 100 pM and 1 nM, respectively, to prepare sample solutions containing the wild type (GGT) probe and the mutant type (GTT) decoy nucleic acid.

Hybrids were formed by denaturing the prepared sample solutions by heating for 5 minutes at 94° C., followed by lowering the temperature at the rate of 0.1° C./second and treating at a constant temperature of 68.8° C. for 5 minutes.

A solution obtained by diluting PicoGreen (Molecular Probes, Inc.) by a factor of 1000 with the aforementioned Tris buffer was respectively added to these concentrated sample solutions to prepare 10-fold dilutions of the concentrated sample solutions, which were then used as sample solutions.

The sample solutions were allowed to stand for 30 minutes or more after adding the diluted PicoGreen solution.

Figure 16:
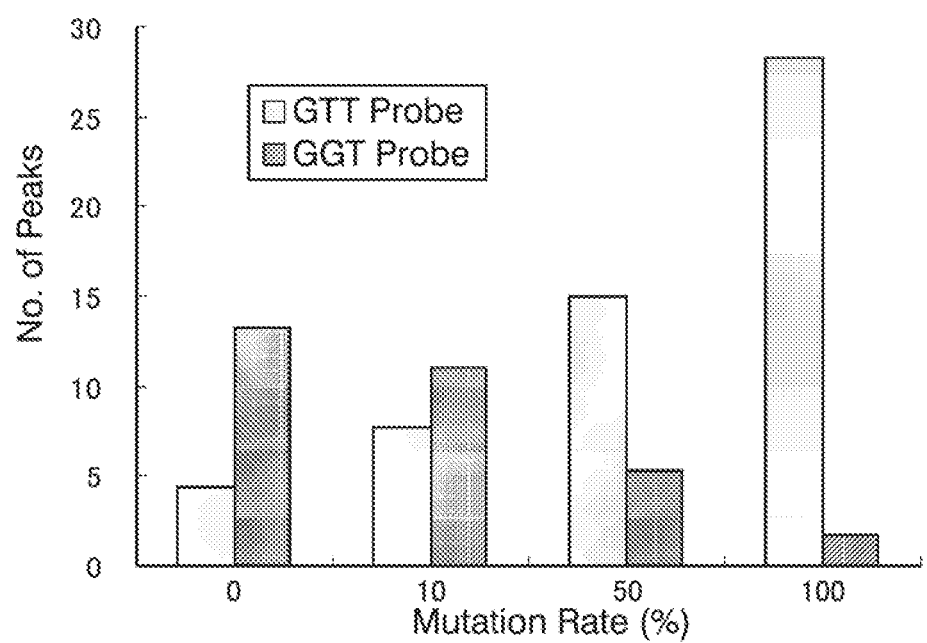
FIG. 16 is a drawing indicating the values of the number or counted peaks of hybrids containing a mutant (GTT) probe and hybrids containing a wild type (GGT) probe for each mutation rate of target nucleic acid molecules added to sample solutions in Example 8.

The numbers of molecules of hybrids containing the mutant type (GTT) probe or the number of hybrids containing the wild type (GGT) probe in the sample solutions were counted by the scanning molecule counting method in the condition same as Example 7. FIG. 16 indicates values for the numbers of counted peaks of hybrids containing the mutant type (GTT) probe (indicated by "GTT Probe" in the drawing) and hybrids containing the wild type (GGT) probe (indicated by "GGT Probe" in the drawing) for each mutation rate of the target nucleic acid molecules added to the sample solutions. As a result, in the sample solutions containing the mutant type (GTT) probe and the wild type (GGT) decoy nucleic acid, the resulting number of peaks increased the higher the mutation rate (namely, the higher the concentration of mutant type (GTT) nucleic acid in the sample solutions), and the amount of hybrids containing the mutant type (GTT) probe was determined to increase. Similarly, in the sample solutions containing the wild type (GGT) probe and the mutant type (GTT) decoy nucleic acid, the resulting number of peaks increased the lower the mutation rate (namely, the higher the concentration of wild type (GGT) nucleic acid in the sample solutions), and the amount of hybrids containing the wild type (GGT) probe was determined to increase. On the basis of these results, the method for identifying polymorphism of nucleic acid molecules of the present invention was clearly able to identify polymorphism even in the case of extremely similar nucleic acid molecules differing by only a single base.

Example 9

The effect of the base pair length of a double-stranded structure in a hybrid was investigated in the case of using a nucleic acid probe and fluorescent intercalator and counting the number of hybrids containing the nucleic acid probe.

First, PCR products having different strand lengths of 100 bp, 200 bp, 400 bp, 800 bp and 1.5 kbp were prepared using a nucleotide in which the 5'-terminal was modified with Rox, a unlabeled nucleotide and AmpliTaq Gold (Applied Biosystems, Inc.) and using plasmid pUC19 (Takara Bio Inc.) as template. Primers were removed from these PCR products using the Wizard V Gel and PCR Clean-Up System (Promega Corp.) followed by measurement of the presence or absence and concentrations of the PCR products by electrophoresis using a bioanalyzer (Agilent Technologies, Inc.). These PCR products (fluorescence-labeled) consisted of hybrids of a single-stranded nucleic acid molecule labeled with Rox on the 5'-terminal thereof and an unlabeled single-stranded nucleic acid molecule.

PCR products (unlabeled) in the form of hybrids consisting of unlabeled single-stranded nucleic acid molecules were obtained in the same manner as described above with the exception of using an oligonucleotide not labeled on the 5'-terminal thereof instead of the oligonucleotide labeled with Rox on the 5'-terminal thereof.

Subsequently, each PCR product was prepared to a concentration of 100 pM using Tris buffer (10 mM Tris-HCl, 1 mM EDTA and 100 mM NaCl, pH 8.0). The prepared PCR product solutions were added to PicoGreen solution (Invitrogen GmbH) diluted 10000-fold with the aforementioned Tris buffer at an arbitrary concentration for use as sample solutions.

The sample solutions were allowed to stand for 30 minutes or more after adding the diluted PicoGreen solution.

Subsequently, the number of molecules of PCR products in the sample solutions was counted according to the scanning molecule counting method under the same conditions as Example 7. As a result, a difference occurred between the number of peaks measured from the fluorescence-labeled PCR products and the number of peaks measured from the unlabeled PCR products according to the strand length of the PCR products. The resulting differences in the number of peaks became smaller as the strand length of the PCR products became longer. This result is thought to be the result of an increase in pulse intensity of the intercalator as strand length increased, thereby resulting in the generation of peaks as non-specific signals in regions at longer wavelengths than the inherent fluorescence wavelength of the intercalator. Conversely, shorter strand lengths result in fewer non-specific signals. On the basis of these results, a strength length of about 400 bp or less can be considered to enable adequate reduction of non-specific signals.

Brief Description of the Reference Symbols

1: Photometric analysis device (confocal microscope)
2: Light source
3: Single-mode optic fiber
4: Collimator lens
5: Dichroic mirror
6, 7, 11: Reflecting mirror
8: Object lens
9: Microplate
10: Well (sample solution container)
12: Condenser lens
13: Pinhole
14: Barrier filter
15: Multi-mode optic fiber
16: Photodetector
17: Mirror deflector
17a: Stage repositioning device
18: Computer

The invention claimed is:

1. A method for identifying a polymorphism of nucleic acid molecules comprising:

(a) preparing a sample solution comprising a first nucleic acid probe, which specifically hybridizes with a single-stranded nucleic acid molecule including a first type of base sequence in a polymorphic sequence, and a target nucleic acid molecule;

(b) forming a hybrid of the nucleic acid molecules in the sample solution prepared in (a);

(c) calculating a number of molecules of the hybrid including the first nucleic acid probe in the sample solution prepared in (a) after carrying out (b);

(d) identifying a polymorphism of the target nucleic acid molecule based on a result of (c);

(e) moving a location of a photodetection region of an optics system in the sample solution in (c) using an optics system of a confocal microscope or a multiphoton microscope;

(f) detecting fluorescence emitted from the hybrid in the photodetection region while moving the location of the photodetection region of the optics system in the sample solution in (c);

(g) individually detecting the hybrid in (c) by individually detecting an optical signal from each hybrid among the detected fluorescent light; and (h) counting a number of particles detected during movement of the location of the photodetection region in (c) by counting the number of individually detected hybrid, wherein the sample solution in (a) or the sample solution after (b) and before (c) includes an oligonucleotide having a base sequence complementary to a base sequence different from the first type of base sequence in the polymorphic sequence.

2. The method for identifying a polymorphism of nucleic acid molecules according to claim 1, wherein the first nucleic acid probe is labeled by a fluorescent substance.

3. The method for identifying a polymorphism of nucleic acid molecules according to claim 2, wherein the sample solution in (a) further comprises a fluorescent double-stranded nucleic acid-binding substance, wherein at least one of the fluorescent substance used to label the first nucleic acid probe and the fluorescent double-stranded nucleic acid-binding substance is a fluorescent substance serving as an energy donor in a fluorescent energy transfer phenomenon, while the other is a substance serving as an energy acceptor in a fluorescent energy transfer phenomenon, and wherein the fluorescence emitted from the hybrid including the first nucleic acid probe in (c) is fluorescence emitted by a fluorescent energy transfer phenomenon occurring between the fluorescent substance used to label the first nucleic acid probe and the fluorescent double-stranded nucleic acid-binding substance.

4. The method for identifying a polymorphism of nucleic acid molecules according to claim 2, wherein the first nucleic acid probe is bound to a fluorescent substance serving as an energy donor and a substance serving as an energy acceptor so that fluorescent energy transfer occurs when the probe is present alone, and fluorescent energy transfer does not occur when the probe hybridizes with another single-stranded nucleic acid molecule, and wherein the fluorescence emitted from the hybrid including the nucleic acid probe is fluorescence that is emitted from the fluorescent substance serving as an energy donor.

5. The method for identifying a polymorphism of nucleic acid molecules according to claim 1, wherein the sample solution in (a) further comprises a fluorescent double-stranded nucleic acid-binding substance that binds specifically to double-stranded nucleic acids.

6. The method for identifying a polymorphism of nucleic acid molecules according to claim 1, wherein the location of the photodetection region is moved at a predetermined speed in moving the location of a photodetection region.

7. The method for identifying a polymorphism of nucleic acid molecules according to claim 1, wherein the location of the photodetection region is moved at a speed faster than a speed of spreading diffusion of the hybrid in moving a location of a photodetection region.

8. The method for identifying a polymorphism of nucleic acid molecules according to claim 1, wherein entry of the hybrid into the photodetection region is detected based on a waveform of the optical signal detected chronologically in individually detecting a hybrid by individually detecting an optical signal from each hybrid among the detected fluorescent light.

9. The method for identifying a polymorphism of nucleic acid molecules according to any of claim 1, wherein the sample solution contains one or more of compounds selected from the group consisting of surfactant, formamide, dimethylsulfoxide and urea.

10. The method for identifying a polymorphism of nucleic acid molecules according to claim 1, wherein (b) is carried out by hybridizing the nucleic acid molecules in the sample solution by lowering a liquid temperature of the sample solution at a lowering rate of 0.05° C./second or faster after denaturing nucleic acid molecules in the sample solution prepared in (a) by heating the sample solution to 70° C. or higher.

11. The method for identifying a polymorphism of nucleic acid molecules according to claim 1, wherein the first nucleic acid probe is composed by binding two or more molecules selected from the group consisting of DNA, RNA and nucleic acid analogues.

12. The method for identifying a polymorphism of nucleic acid molecules according to any of claim 1, wherein the polymorphic sequence is a base sequence comprising a polymorphic site of a genetic polymorphism or a base sequence comprising a mutation site of a somatic mutation.

13. The method for identifying a polymorphism of nucleic acid molecules according to claim 12, wherein the somatic mutation is a mutation of the K-ras gene.

* * * * *

SEQUENCE LISTING

<160> NUMBER OF SEQ ID NOS: 12

<210> SEQ ID NO 1
<211> LENGTH: 28
<212> TYPE: DNA

```
<213> ORGANISM: Artificial Sequence
<220> FEATURE:
<223> OTHER INFORMATION: Description of Artificial Sequence: Molecular
      beacon probe for K-ras GTT-mutant.

<400> SEQUENCE: 1
cctacgccaa cagctccaac tacgtagg                                        28

<210> SEQ ID NO 2
<211> LENGTH: 45
<212> TYPE: DNA
<213> ORGANISM: Homo sapiens

<400> SEQUENCE: 2
tgactgaata taaacttgtg gtagttggag ctggtggcgt aggca                     45

<210> SEQ ID NO 3
<211> LENGTH: 45
<212> TYPE: DNA
<213> ORGANISM: Homo sapiens

<400> SEQUENCE: 3
tgactgaata taaacttgtg gtagttggag ctgttggcgt aggca                     45

<210> SEQ ID NO 4
<211> LENGTH: 23
<212> TYPE: DNA
<213> ORGANISM: Homo sapiens

<400> SEQUENCE: 4
cctacgccac cagctccaac tac                                             23

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Molecular
      beacon probe for K-ras (wild type).

<400> SEQUENCE: 5
cctacgccac cagctccaac tacgtagg                                        28

<210> SEQ ID NO 6
<211> LENGTH: 23
<212> TYPE: DNA
<213> ORGANISM: Homo sapiens

<400> SEQUENCE: 6
cctacgccaa cagctccaac tac                                             23

<210> SEQ ID NO 7
<211> LENGTH: 22
<212> TYPE: DNA
<213> ORGANISM: Homo sapiens

<400> SEQUENCE: 7
cctacgccac cagctccaac ta                                              22

<210> SEQ ID NO 8
<211> LENGTH: 22
<212> TYPE: DNA
<213> ORGANISM: Homo sapiens

<400> SEQUENCE: 8
```

```
cctacgccaa cagctccaac ta                                    22

<210> SEQ ID NO 9
<211> LENGTH: 37
<212> TYPE: DNA
<213> ORGANISM: Homo sapiens

<400> SEQUENCE: 9
tctgaattag ctgtatcgtc aaggcactct tgcctac                    37

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Molecular
      beacon probe for K-ras (common).

<400> SEQUENCE: 10
gccttgacga tacagctaat tcaaggc                               27

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Probe
      for K-ras GTT-mutant.

<400> SEQUENCE: 11
cctacgccaa cagctccaac tac                                   23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Probe
      for K-ras (wild type).

<400> SEQUENCE: 12
cctacgccac cagctccaac tac                                   23
```